United States Patent
Freeman et al.

(10) Patent No.: US 10,799,177 B2
(45) Date of Patent: Oct. 13, 2020

(54) ESTIMATION OF ADIPOSE TISSUE WITH A MODIFIED NEAR INFRARED SPECTRAL SENSOR

(71) Applicant: ZOLL Medical Corporation, Chelmsford, MA (US)

(72) Inventors: Gary A. Freeman, Waltham, MA (US); Ulrich Herken, Medford, MA (US); Christopher L. Kaufman, Somerville, MA (US); Annemarie Elizabeth Silver, Bedford, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 636 days.

(21) Appl. No.: 15/077,385

(22) Filed: Mar. 22, 2016

(65) Prior Publication Data

US 2016/0278699 A1    Sep. 29, 2016

Related U.S. Application Data

(60) Provisional application No. 62/137,741, filed on Mar. 24, 2015.

(51) Int. Cl.
*A61B 5/048*    (2006.01)
*A61B 5/00*    (2006.01)
(Continued)

(52) U.S. Cl.
CPC .......... *A61B 5/4872* (2013.01); *A61B 5/0075* (2013.01); *A61B 5/14551* (2013.01); *A61B 8/085* (2013.01); *A61B 8/0858* (2013.01); *A61B 5/0022* (2013.01); *A61B 5/0537* (2013.01); *A61B 5/14535* (2013.01); *A61B 5/14539* (2013.01); *A61B 5/7275* (2013.01); *A61B 5/7282* (2013.01); *A61B 2562/0219* (2013.01)

(58) Field of Classification Search
CPC ..... A61B 5/681; A61B 5/0537; A61B 5/4872; A61B 5/0022; A61B 5/02055
See application file for complete search history.

(56) References Cited

U.S. PATENT DOCUMENTS 9,259,342 B2 *    2/2016    Wong ................... A61F 5/0026
2011/0205535 A1 *    8/2011    Soller ............... A61B 5/14552
356/300

(Continued)

*Primary Examiner* — Michael J D Abreu
(74) *Attorney, Agent, or Firm* — Fish & Richardson P.C.

(57) ABSTRACT

A system for non-invasively measuring a physiologic status patient tissue according to an embodiment includes a housing; an optical spectroscope with a wavelength-sensitive sensor capable of detecting light intensity, at two or more distinct wavelengths, of light scattered and/or reflected by muscle tissue of the patient in order to measure a physiologic status of the muscle tissue, a bioimpedance sensor at least partially disposed within the housing, the bioimpedance sensor configured to generate a signal corresponding to an estimation of a thickness of an adipose tissue layer between the optical spectroscope and the muscle tissue, and a processor configured to (1) receive the estimations of the thickness, (2) compare the estimations of the thickness, and (3) based on the comparison, generate a visual indication configured to assist in placement of the housing toward or at a location corresponding to the smaller or smallest thickness of the adipose tissue layer.

29 Claims, 13 Drawing Sheets

(51) Int. Cl.
    *A61B 8/08*     (2006.01)
    *A61B 5/1455*     (2006.01)
    *A61B 5/053*     (2006.01)
    *A61B 5/145*     (2006.01)

(56) References Cited

U.S. PATENT DOCUMENTS

| | | | |
|---|---|---|---|
| 2013/0060103 A1* | 3/2013 | Bergida | A61B 5/0031 600/302 |
| 2013/0158634 A1* | 6/2013 | Ron Edoute | A61N 5/00 607/102 |
| 2014/0039284 A1* | 2/2014 | Niwayama | A61B 5/0059 600/324 |

* cited by examiner

ESTIMATION OF ADIPOSE TISSUE WITH A MODIFIED NEAR INFRARED SPECTRAL SENSOR

CROSS-REFERENCE TO RELATED APPLICATIONS

This application claims the benefit of U.S. Provisional Patent Application Ser. 62/137,741, filed on Mar. 24, 2015, entitled "Estimation of Adipose Tissue with a Modified Near Infrared Spectral Sensor," which is incorporated herein by reference in its entirety for all purposes.

TECHNICAL FIELD

Embodiments of the present invention relate generally to spectral sensors for measuring pH and hematocrit, and more specifically to spectral sensors including a sensor for measuring presence and/or distribution of adipose tissue.

BACKGROUND

Spectral sensors for noninvasive measurement or calculation of oxygen saturation, oxygen tension, pH, hematocrit, hemoglobin concentration, anaerobic threshold, water content, and oxygen consumption are described in the art, for example in U.S. Patent Application Publication No. 2011/0205535, published Aug. 25, 2011 ("the '535 Publication"), the contents of which are incorporated by reference herein in their entirety for all purposes. One such spectral sensor 10 is illustrated in FIGS. 1 and 2, reproduced from the '535 Publication, which show a spectral detector 12, two short-distance radiation sources 14a, 14b, and six long-distance radiation sources 16a-16e. The housing 11 includes a concave inner surface that is configured for placement against a patient's skin above tissue, for example peripheral muscle tissue, which is to be monitored. The housing 11 further includes a handle 15 on each side, as well as apertures 17a, 17b for communications interface. As shown in FIG. 2, the radiation sources 14a, 14b and 16a-16e may be part of a circuit board 18.

However, the effective operation of spectral sensors such as sensor 10 can often be hampered by layers of adipose tissue between the sensor 10 and the tissue to be measured (for example muscle tissue).

SUMMARY

In Example 1, a system for non-invasively measuring a physiologic status of tissue of a patient according to an embodiment of the present invention includes a housing, an optical spectroscope at least partially disposed within the housing, the optical spectroscope comprising at least one light source capable of emitting light at a range of wavelengths, a wavelength-sensitive sensor capable of detecting light intensity, at two or more distinct wavelengths, of light scattered and/or reflected by muscle tissue of the patient in order to measure a physiologic status of the muscle tissue, a bioimpedance sensor at least partially disposed within the housing, the bioimpedance sensor configured to generate a signal corresponding to an estimation of a thickness of an adipose tissue layer between the optical spectroscope and the muscle tissue, and a processor communicably coupled to a memory, the memory including instructions that, when executed by the processor, cause the processor to (1) receive the estimations of the thickness generated upon placement of the housing at two or more locations on the patient, (2) compare the estimations of the thickness, and (3) based on the comparison, generate a visual indication configured to assist in placement of the housing toward or at a location corresponding to thickness of the adipose tissue layer that is smaller relative to surrounding thicknesses.

In Example 2, the system of Example 1, further comprising a visual indicator disposed on or within the housing, wherein the memory includes instructions that, when executed by the processor, cause the processor to generate the visual indication by illuminating the visual indicator.

In Example 3, the system of any of Examples 1 or 2, wherein the visual indication is a directional indication.

In Example 4, the system of any of Examples 1-3, wherein the visual indication is a multidirectional indication.

In Example 5, the system of any of Examples 1-4, wherein the housing comprises at least one inertial sensor communicably coupled with the processor and configured to provide positioning or location information to the processor.

In Example 6, the system of any of Examples 1-5, wherein the inertial sensor comprises one or both of an accelerometer and a gyroscope.

In Example 7, a system for non-invasively measuring a physiologic status of tissue of a patient according to an embodiment of the present invention includes a cuff configured to at least partially cover a portion of a limb; a first bioimpedance sensor disposed on the cuff so as to abut skin of the patient when the cuff at least partially covers the portion of the limb, the first bioimpedance sensor configured to generate a signal corresponding to an estimation of a thickness of an adipose tissue layer at a first location; a second bioimpedance sensor disposed on the cuff so as to be separated from the first bioimpedance sensor and to abut skin of the patient when the cuff at least partially covers the portion of the limb, the second bioimpedance sensor configured to generate a signal corresponding to an estimation of a thickness of an adipose tissue layer at a second location; a first visual indicator disposed on the cuff in manner corresponding to the first location; a second visual indicator disposed on the cuff in a manner corresponding to the second location; and a processor communicably coupled to a memory, the first and second bioimpedance sensors, and the first and second visual indicators, the memory including instructions that, when executed by the processor, cause the processor to (1) receive the estimations of the thickness of the adipose tissue layer at the first and second locations, (2) compare the estimations of the thickness, and (3) based on the comparison, activating the first visual indicator when the comparison indicates that the estimation of the thickness of the adipose tissue layer at the first location is lower than the estimation of the thickness of the adipose tissue layer at the second location.

In Example 8, the system of any of Examples 1-7, wherein the first and second locations are circumferentially offset about the limb when the cuff at least partially covers the portion of the limb.

In Example 9, the system of any of Examples 1-8, wherein the first visual indicator and the first bioimpedance sensor are substantially aligned at a first circumferential position about the limb when the cuff at least partially covers the portion of the limb, and wherein the second visual indicator and the second bioimpedance sensor are substantially aligned at a second circumferential position about the limb when the cuff at least partially covers the portion of the limb, and wherein the first and second circumferential positions are offset circumferentially.

In Example 10, the system of any of Examples 1-9, further comprising an optical spectroscope, the optical spectroscope configured for placement on the patient at the first location based on the activation of the first visual indicator.

In Example 11, the system of any of Examples 1-10, further comprising: a third bioimpedance sensor disposed on the cuff so as to be separated from the first and second bioimpedance sensors and to abut skin of the patient when the cuff at least partially covers the portion of the limb, the third bioimpedance sensor configured to generate a signal corresponding to an estimation of a thickness of an adipose tissue layer at a third location; a fourth bioimpedance sensor disposed on the cuff so as to be separated from the first, second, and third bioimpedance sensors and to abut skin of the patient when the cuff at least partially covers the portion of the limb, the fourth bioimpedance sensor configured to generate a signal corresponding to an estimation of a thickness of an adipose tissue layer at a fourth location; a fifth bioimpedance sensor disposed on the cuff so as to be separated from the first, second, third, and fourth bioimpedance sensors and to abut skin of the patient when the cuff at least partially covers the portion of the limb, the fifth bioimpedance sensor configured to generate a signal corresponding to an estimation of a thickness of an adipose tissue layer at a fifth location; a third visual indicator disposed on the cuff in manner corresponding to the third location; a fourth visual indicator disposed on the cuff in a manner corresponding to the fourth location; a fifth visual indicator disposed on the cuff in a manner corresponding to the fourth location; and wherein the memory further includes instructions that, when executed by the processor, cause the processor to (1) receive the estimations of the thickness of the adipose tissue layer at the third, fourth, and fifth locations, and (3) based on the comparison, activating the first visual indicator when the comparison indicates that the estimation of the thickness of the adipose tissue layer at the first location is lower than the estimation of the thickness of the adipose tissue layer at the second, third, fourth, and fifth locations.

In Example 12, a system for non-invasively measuring a physiologic status of tissue of a patient according to an embodiment of the present invention includes a housing; an optical spectroscope at least partially disposed within the housing, the optical spectroscope comprising at least one light source capable of emitting light at a range of wavelengths, a wavelength-sensitive sensor capable of detecting light intensity, at two or more distinct wavelengths, of light scattered and/or reflected by muscle tissue of the patient in order to measure a physiologic status of the muscle tissue; and a mechanical adipose sensor at least partially disposed on the housing, the mechanical adipose sensor configured to generate a signal corresponding to an estimation of a thickness of an adipose tissue layer between the optical spectroscope and the muscle tissue; and a processor communicably coupled to a memory, the memory including instructions that, when executed by the processor, cause the processor to (1) receive the estimations of the thickness generated upon placement of the housing at two or more locations on the patient, (2) compare the estimations of the thickness, and (3) based on the comparison, generate a visual indication configured to assist in placement of the housing toward or at a location corresponding to thickness of the adipose tissue layer that is smaller relative to surrounding thicknesses.

In Example 13, the system of any of Examples 1-12, wherein the mechanical adipose sensor is a skin fold caliper.

In Example 14, the system of any of Examples 1-13, wherein the mechanical adipose sensor is a spring loaded skin probe.

In Example 15, the system of any of Examples 1-14, further comprising a visual indicator disposed on or within the housing, wherein the memory includes instructions that, when executed by the processor, cause the processor to generate the visual indication by illuminating the visual indicator.

In Example 16, the system of any of Examples 1-15, wherein the visual indication is a directional indication.

In Example 17, the system of any of Examples 1-16, wherein the visual indication is a multidirectional indication.

In Example 18, the system of any of Examples 1-17, wherein the housing comprises at least one inertial sensor communicably coupled with the processor and configured to provide positioning or location information to the processor.

In Example 19, the system of any of Examples 1-18, wherein the inertial sensor comprises one or both of an accelerometer and a gyroscope.

In Example 20, a system for non-invasively measuring a physiologic status of tissue of a patient according to an embodiment of the present invention includes a housing; an optical spectroscope at least partially disposed within the housing, the optical spectroscope comprising at least one light source capable of emitting light at a range of wavelengths, a wavelength-sensitive sensor capable of detecting light intensity, at two or more distinct wavelengths, of light scattered and/or reflected by muscle tissue of the patient in order to measure a physiologic status of the muscle tissue; and an ultrasound sensor at least partially disposed within the housing, the ultrasound sensor configured to generate a signal corresponding to an estimation of a thickness of an adipose tissue layer between the optical spectroscope and the muscle tissue; and a processor communicably coupled to a memory, the memory including instructions that, when executed by the processor, cause the processor to (1) receive the estimations of the thickness generated upon placement of the housing at two or more locations on the patient, (2) compare the estimations of the thickness, and (3) based on the comparison, generate a visual indication configured to assist in placement of the housing toward or at a location corresponding to thickness of the adipose tissue layer that is smaller relative to surrounding thicknesses.

In Example 21, the system of any of Examples 1-20, further comprising a visual indicator disposed on or within the housing, wherein the memory includes instructions that, when executed by the processor, cause the processor to generate the visual indication by illuminating the visual indicator.

In Example 22, the system of any of Examples 1-21, wherein the visual indication is a directional indication.

In Example 23, the system of any of Examples 1-22, wherein the visual indication is a multidirectional indication.

In Example 24, the system of any of Examples 1-23, wherein the housing comprises at least one inertial sensor communicably coupled with the processor and configured to provide positioning or location information to the processor.

In Example 25, the system of any of Examples 1-24, wherein the inertial sensor comprises one or both of an accelerometer and a gyroscope.

In Example 26, a system for non-invasively measuring a physiologic status of tissue of a patient according to an embodiment of the present invention includes a housing; an optical spectroscope at least partially disposed within the housing, the optical spectroscope comprising at least one light source capable of emitting light at a range of wavelengths, a wavelength-sensitive sensor capable of detecting light intensity, at two or more distinct wavelengths, of light scattered and/or reflected by muscle tissue of the patient in order to measure a physiologic status of the muscle tissue; and a body mass index (BMI) calculator at least partially disposed within the housing, the BMI calculator configured to receive user input and to generate a signal corresponding to an estimation of a thickness of an adipose tissue layer between the optical spectroscope and the muscle tissue; and a processor communicably coupled to a memory, the memory including instructions that, when executed by the processor, cause the processor to (1) receive the estimation of the thickness of the adipose tissue layer, and (2) adjust the measurement of the physiologic status of the muscle tissue based on the estimation of the thickness of the adipose tissue layer.

In Example 27, a method for sensing adipose tissue in the use of a spectral sensor on a patient according to an embodiment of the present invention includes placing a spectral sensor against skin of the patient above muscle tissue of the patient, wherein the spectral sensor comprises two or more long-distance radiation sources, one or more short-distance radiation sources, and a spectral detector, at least two of the two or more long-distance radiation sources and at least one of the one or more short-distance radiation sources located on the spectral sensor at different distances from the spectral detector, and wherein the spectral sensor further comprises a bioimpedance sensor; estimating, using the bioimpedance sensor, a thickness of an adipose tissue layer between the spectral sensor and the muscle tissue; and selecting one of the at least two or more long-distance radiation sources to illuminate the muscle tissue based on the estimation of the thickness of the adipose tissue layer.

In Example 28, the method of any of Examples 1-27, wherein estimating the thickness comprises using the bioimpedance sensor to estimate a body mass index of the patient, and correlating the body mass index to a value in a lookup table for fat thicknesses.

In Example 29, the method of any of Examples 1-28, wherein estimating the thickness comprises reconciling adipose thickness estimations from the bioimpedance sensor with adipose thickness estimations from the spectral sensor.

In Example 30, the method of any of Examples 1-29, further comprising moving the spectral sensor from a first position against the skin of the patient to a second position against the skin of the patient, and estimating, using the bioimpedance sensor, a thickness of an adipose tissue layer at the second position between the spectral sensor and the muscle tissue.

In Example 31, the method of any of Examples 1-30, further comprising determining whether the adipose tissue layer at the second position is thicker than the adipose tissue layer at the first position.

In Example 32, the method of any of Examples 1-31, further comprising using a visual indicator to a direct positioning of the spectral sensor from a first position against the skin of the patient to a second position against the skin of the patient, the second position having a thinner adipose tissue layer than the first position.

In Example 33, the method of any of Examples 1-32, wherein utilizing the visual indicator includes estimating, using the bioimpedance sensor, a thickness of an adipose tissue layer while translating the spectral sensor from the first position against the skin of the patient to the second position against the skin of the patient.

In Example 34, the method of any of Examples 1-33, further comprising adjusting defibrillation energy of a defibrillator based on the estimation of the thickness of the adipose tissue layer.

In Example 35, the method of any of Examples 1-34, further comprising using an audio or visual indicator to designate a level of force applied to hold the spectral sensor against skin of the patient.

In Example 36, a system for non-invasively measuring a physiologic status of tissue of a patient according to an embodiment of the present invention includes a housing; an optical spectroscope at least partially disposed within the housing, the optical spectroscope comprising at least one light source capable of emitting light at a range of wavelengths, a wavelength-sensitive sensor capable of detecting light intensity, at two or more distinct wavelengths, of light scattered and/or reflected by muscle tissue of the patient in order to measure a physiologic status of the muscle tissue; an ultrasound sensor at least partially disposed within the housing, the ultrasound sensor configured to generate a signal corresponding to an estimation of a thickness of an adipose tissue layer between the optical spectroscope and the muscle tissue; and a processor communicably coupled to a memory, the memory including instructions that, when executed by the processor, cause the processor to (1) receive the estimations of the thickness generated upon placement of the housing at two or more locations on the patient, (2) compare the estimations of the thickness, and (3) based on the comparison, generate a visual indication configured to assist in placement of the housing toward or at a location corresponding to thickness of the adipose tissue layer that is smaller relative to surrounding thicknesses.

In Example 37, a method for sensing adipose tissue in the use of a spectral sensor on a patient according to an embodiment of the present invention includes placing a spectral sensor against skin of the patient above muscle tissue of the patient, wherein the spectral sensor comprises two or more long-distance radiation sources, one or more short-distance radiation sources, and a spectral detector, at least two of the two or more long-distance radiation sources and at least one of the one or more short-distance radiation sources located on the spectral sensor at different distances from the spectral detector, and wherein the spectral sensor further comprises a bioimpedance sensor; estimating, using the bioimpedance sensor, a thickness of an adipose tissue layer between the spectral sensor and the muscle tissue; and adjusting a frequency of one of the at least two or more long-distance radiation sources to illuminate the muscle tissue based on the estimation of the thickness of the adipose tissue layer.

In Example 38, the method of any of Examples 1-37, wherein estimating the thickness comprises using the bioimpedance sensor to estimate a body mass index of the patient, and correlating the body mass index to a value in a lookup table for fat thicknesses.

In Example 39, the method of any of Examples 1-38, wherein estimating the thickness comprises using the bioimpedance sensor to estimate a body mass index of the patient, and correlating the body mass index to a value in a lookup table for fat thicknesses.

In Example 40, the method of any of Examples 1-39, wherein estimating the thickness comprises using a caliper to estimate a body mass index of the patient, and correlating the body mass index to a value in a lookup table for fat thicknesses.

In Example 41, the method of any of Examples 1-40, wherein the caliper is coupled with the spectral sensor.

In Example 42, the method of any of Examples 1-41, wherein estimating the thickness and adjusting the frequency occurs simultaneously.

In Example 43, the method of any of Examples 1-42, further comprising using a pressure sensor to determine a level of force applied to hold the spectral sensor against skin of the patient.

In Example 44, the method of any of Examples 1-43, further comprising adjusting the estimation of the thickness of the adipose tissue layer based on the determined level of force applied to hold the spectral sensor against skin of the patient.

In Example 45, the method of any of Examples 1-44, further including using a visual indicator to direct a positioning of the spectral sensor from a first position against the skin of the patient to a second position against the skin of the patient, the second position having a thinner adipose tissue layer than the first position, and estimating, using the bioimpedance sensor, a thickness of an adipose tissue layer while translating the spectral sensor from the first position against the skin of the patient to the second position against the skin of the patient.

In Example 46, a system for estimating adipose tissue thickness of a patient according to an embodiment of the present invention includes a spectral sensor including a surface configured to interface against skin of the patient above muscle tissue of the patient; two or more long-distance radiation sources configured to illuminate the muscle tissue; one or more short-distance radiation sources configured to illuminate the muscle tissue; a spectral detector configured to measure radiation sources as reflected by the muscle tissue, wherein the at least two of the two or more long-distance radiation sources and at least one of the one or more short-distance radiation sources are located on the spectral sensor at different distances from the spectral detector; a bioimpedance sensor configured to estimate a thickness of an adipose tissue layer between the spectral sensor and the muscle tissue; and a frequency adjuster circuit configured to adjust one of the at least two or more long-distance radiation sources to illuminate the muscle tissue based on the estimation of the thickness of the adipose tissue layer.

In Example 47, the system of any of Examples 1-46, further including a visual indicator configured to a direct positioning of the spectral sensor from a first position against the skin of the patient to a second position against the skin of the patient, the second position having a thinner adipose tissue layer than the first position.

In Example 48, the system of any of Examples 1-47, wherein the bioimpedance sensor is further configured estimate a thickness of an adipose tissue layer while translating the spectral sensor from the first position against the skin of the patient to the second position against the skin of the patient.

In Example 49, the system of any of Examples 1-48, further comprising a processor circuit configured to select one of the at least two or more long-distance radiation sources to illuminate the muscle tissue based on the estimation of the thickness of the adipose tissue layer.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
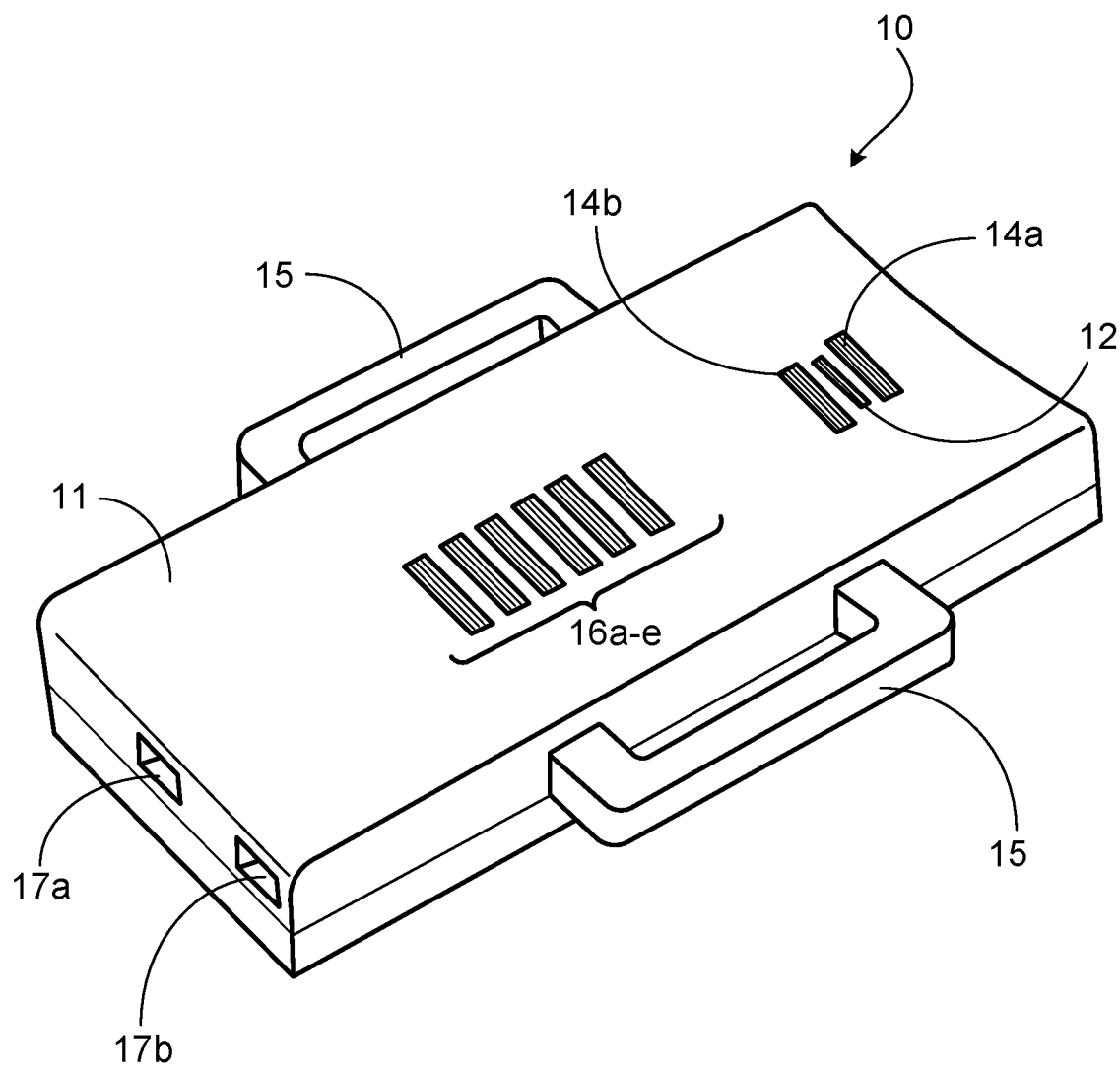
FIG. 1 illustrates a prior art spectral sensor.
Figure 2:
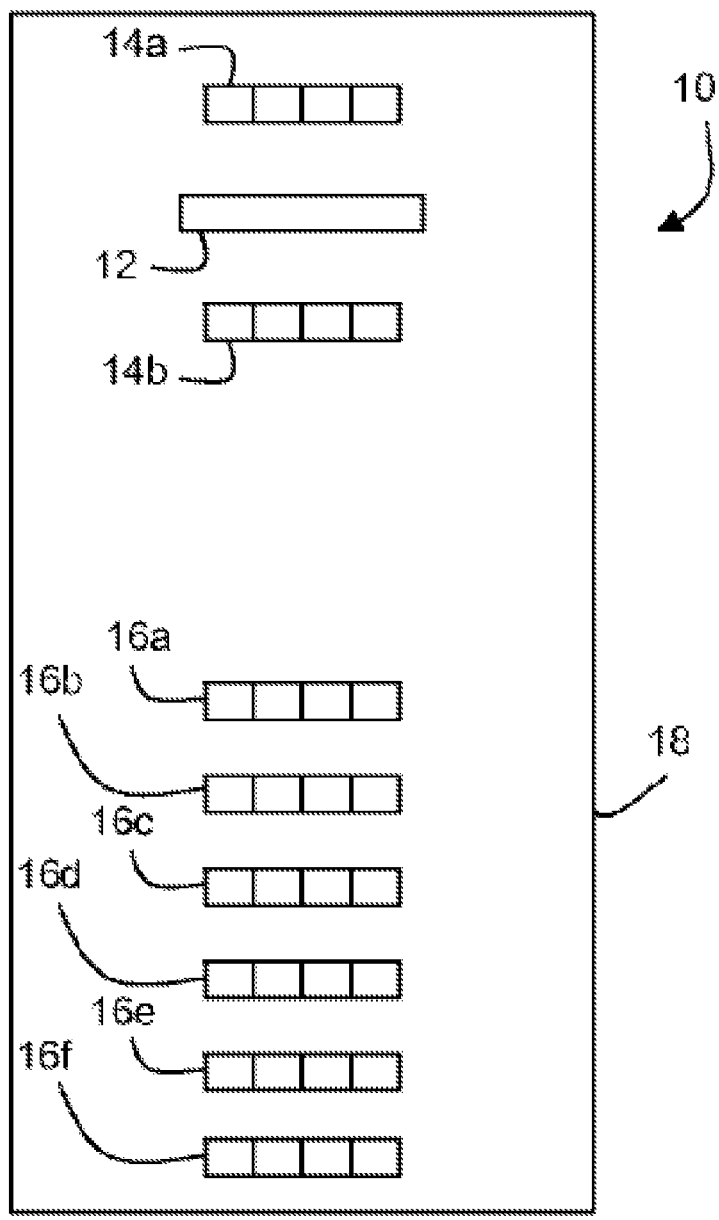
FIG. 2 illustrates a bottom schematic view of placement of radiation sources and a detector of the prior art spectral sensor of FIG. 1.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

There are several different implementations of the invention possible. Some possible implementations are described herein; however, as one of ordinary skill in the art would appreciate, these are exemplary implementations of the invention, which is not limited to the detailed examples provided.

An embodiment of the invention includes a patient monitoring and control system including a spectral sensor and an adipose sensor. The spectral sensor may include a muscle oxygen saturation sensor, a pH sensor, a blood hematocrit sensor, an end-tidal carbon dioxide sensor, and/or other sensors capable of obtaining the physiological status of a tissue of a patient. Such physiological status may include tissue oxygen saturation, pH, hematocrit level, carbon dioxide levels, and the like. The spectral sensor may be communicably coupled with a patient monitor, which may be a defibrillator or an automatic external defibrillator, a standalone monitor, a hand held monitor, a remote monitor, and/or the like. A patient monitor may include or otherwise be in communication with a processor, which is configured to or otherwise capable of executing all or parts of the methods described herein and/or described in the '535 Publication. As used herein, "adipose sensor" is used in its broadest sense to refer to a sensor configured to estimate adipose tissue layer thickness. The adipose sensor may include a bioimpedance sensor, an ultrasound sensor, a body mass index (BMI) calculator, and/or a mechanical adipose sensor (e.g. a caliper-based sensor).

Figure 3:
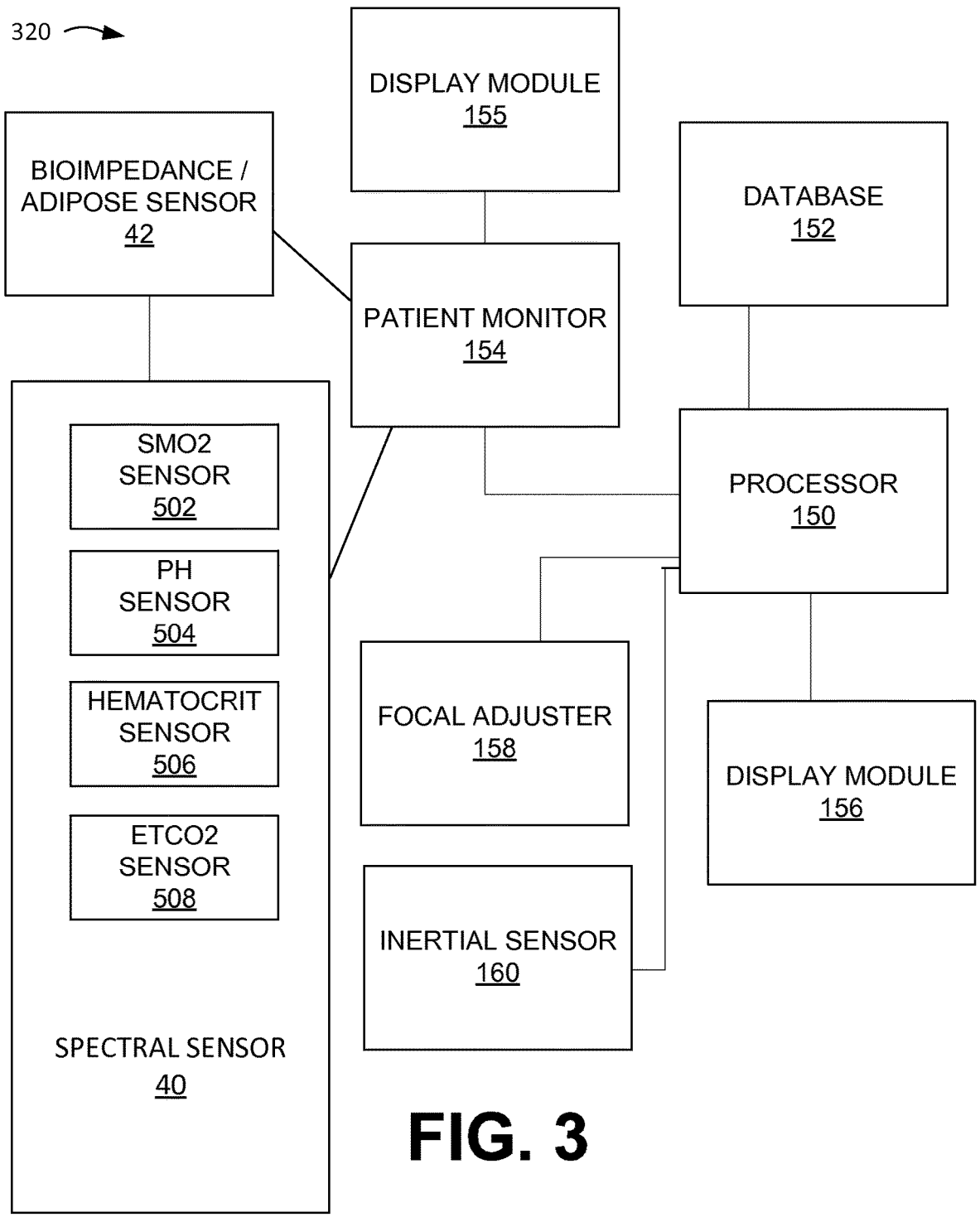
FIG. 3 illustrates a patient monitoring and control system including a spectral sensor and bioimpedance sensor, according to embodiments of the present invention.

FIG. 3 illustrates one example of such a patient monitoring and control system 320 including a spectral sensor 40 and bioimpedance sensor 42, according to embodiments of the present invention. The spectral sensor 40, which may have (or its hardware is capable of) a muscle oxygen saturation sensor 502, a pH sensor 504, a blood hematocrit sensor 506, and/or an end-tidal carbon dioxide sensor 508, according to embodiments of the present invention. Sensor 40 is communicably coupled with a patient monitor 154, which may be, for example, a defibrillator or an automatic external defibrillator, according to embodiments of the present invention. Patient monitor 154 may include or otherwise by in communication with a processor 150, which is configured to or otherwise capable of executing all or parts of the methods described herein and/or described in the '535 Publication. A database 152 may be used to store information and/or instructions or other software. The patient monitor 154 may have its own display module 155 in communication therewith, and/or the system 320 may include a separate display module 156, according to embodiments of the present invention.

Figure 6:
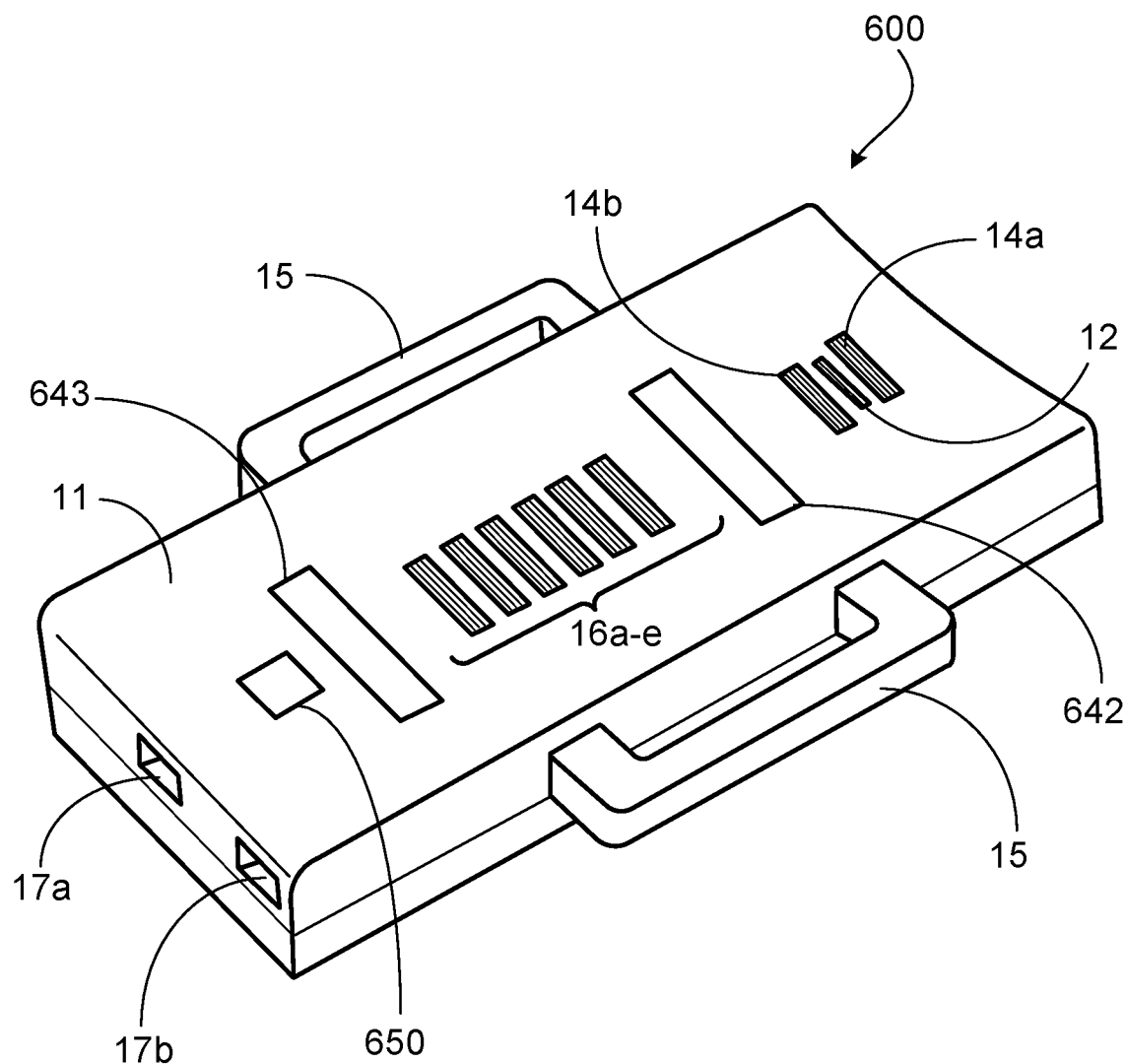
FIG. 6 illustrates a bottom perspective view of a spectral sensor having bioimpedance sensor electrodes and a spectral bench, according to embodiments of the present invention.

The bioimpedance sensor 42 includes two or more electrodes, as is shown in FIG. 6, to estimate the thickness of an adipose tissue layer. Different tissue layers oppose current differently. An alternating current signal is applied and a response from the patient is measured by the two or more electrodes of the bioimpedance sensor 42. Based on the amplitude and/or frequency of the applied alternating current signal, and the response thereto, the processor 150 determines an estimate of the thickness of an adipose tissue layer. As is known, the two or more electrodes of the bioimpedance sensor 42 can apply current levels from 20 µA to 10 mA rms at a frequency range of 20-100 KHz. The database 152, in certain embodiments, stores information that associates tissue composition with a measured response by the bioimpedance sensor 42. The processor 150 is configured to estimate the thickness of the adipose tissue layer based on the measurement by the bioimpedance sensor 42 and the information stored in the database 152.

According to alternative embodiments of the present invention, sensor 42 is an ultrasound sensor which sends sonic energy into the patient and receives data about the sonic response of the underlying tissues, which may be interpreted by sensor 42 and/or by processor 150 to determine the types of tissues and their relative depths below the sensor 42 and/or housing 11, in order to estimate the thickness of an adipose tissue layer.

According to yet other alternative embodiments, adipose sensor 42 is a body mass index (BMI) calculator 42 at least partially disposed within the housing 11, which is configured to receive user input and to generate a signal corresponding to an estimation of a thickness of an adipose tissue layer between the optical spectroscope 40 and the underlying muscle tissue. The BMI calculator 42 may be a circuit which permits user input (e.g. manually or via communication from another system) of user information that may be correlated with the user's BMI and/or with the average thickness of the adipose tissue layer at various locations. The BMI calculator 42 may also be configured to receive input of an indication of the location of the spectral sensor 40 (e.g. biceps, quadriceps, and the like) in order to determine, for example using a lookup table or tables, the estimate of the adipose tissue layer under the sensor 40, according to embodiments of the present invention. The BMI calculator 42 may receive other information to use in calculating or interpolating or extrapolating from lookup data tables, for example patient gender, weight, and height.

The spectral sensor 40, as described in further detail in connection with FIG. 6, can include short-distance radiation sources and long-distance radiation sources. For example, the spectral sensor 600 of FIG. 6 may be similar to the spectral sensor 40, which may be similar to the spectral sensor 10 except modified to include bioimpedance electrodes 642, 643 and/or pressure sensors 650. The short-distance radiation sources and long-distance radiation sources illuminate the patient's tissue, and the reflective response is measured by the spectral sensor 40. Thus, the spectral sensor 40 is configured to estimate the thickness of an adipose tissue layer. However, the composition of body tissue can have an effect on the estimation as fat can be a barrier to accurate measurement. Thus, the position of the short-distance radiation sources and the long-distance radiation sources may be at areas of different effectiveness for estimating the thickness of an adipose tissue layer. Based on the estimation of the thickness of the adipose tissue layer, the processor 150 can select one of the at least two or more long-distance radiation sources to illuminate the muscle tissue. The different positions of one or more of the long-distance radiation sources may be advantageous over others of the long-distance radiation sources due to the composition of the patient's tissue (e.g., more or less fat) under the respective long distance radiation sources. This feedback loop from the processor 150 allows for a determination as to the accuracy of the estimation of the thickness of the adipose tissue layer.

Additionally, information about the adipose tissue measurements determined using sensor 40 may be displayed on the display module 155 of the patient monitor 154 and/or the other display module 156, for example along with other data about a patient to which the sensor 40 is applied, according to embodiments of the present invention. For example, the displayed information may include estimates of thickness of adipose tissue, indications of the presence of adipose tissue, representations of measurements taken over time (e.g., plots, trend graphs, etc.), and/or the like. Such data or information may also be stored in database 152, for example independently or with other information about the patient or the medical encounter for which the spectral sensor's 40 data is being collected. The hardware elements and/or modules shown in FIG. 3 may be included on the same device and/or distributed across multiple devices, and each such hardware element or module shown in FIG. 3 may have its elements or functionality spread across multiple devices.

A focus adjuster 158 is a mechanism that adjusts the focus and/or focal point of the light or radiation emitted by one or more of the long-distance radiation sources 16a-e and/or by the one or more short-distance radiation sources 14a, 14b, according to embodiments of the present invention. The focus adjuster 158 may include an optical lens or series of optical lenses, and/or may include a moveable mechanical relationship between the light source and the housing 10. If the adipose tissue layer is determined to be thicker below a particular radiation source, the focus adjuster 158 can adjust the focal point of that particular radiation source in order to compensate for the adipose tissue layer depth, based on the determination. If the adipose tissue layer is determined to be thinner below a particular radiation source, the focus adjuster 158 can adjust the focal point of that particular radiation source in order to compensate for the adipose tissue layer depth, based on the determination. In this way, the light source(s) may be dynamically adjusted by the focus adjuster 158 based on one or more determinations about adipose tissue layer thicknesses below the housing 10.

An inertial sensor 160 is communicably coupled to processor 150, and is configured to provide location or position information, which may assist the processor in determining where the thinnest adipose tissue layer existed, and/or in guiding the user to place the device toward or at such position after it has been determined or estimated, according to embodiments of the present invention. Inertial sensor 160 may include, for example, a gyroscope and/or an accelerometer, and may be mechanically and/or fixedly coupled with the housing of the bioimpedance/adipose sensor 42 and/or the optical spectroscope sensor 40, according to embodiments of the present invention.

Figure 4:
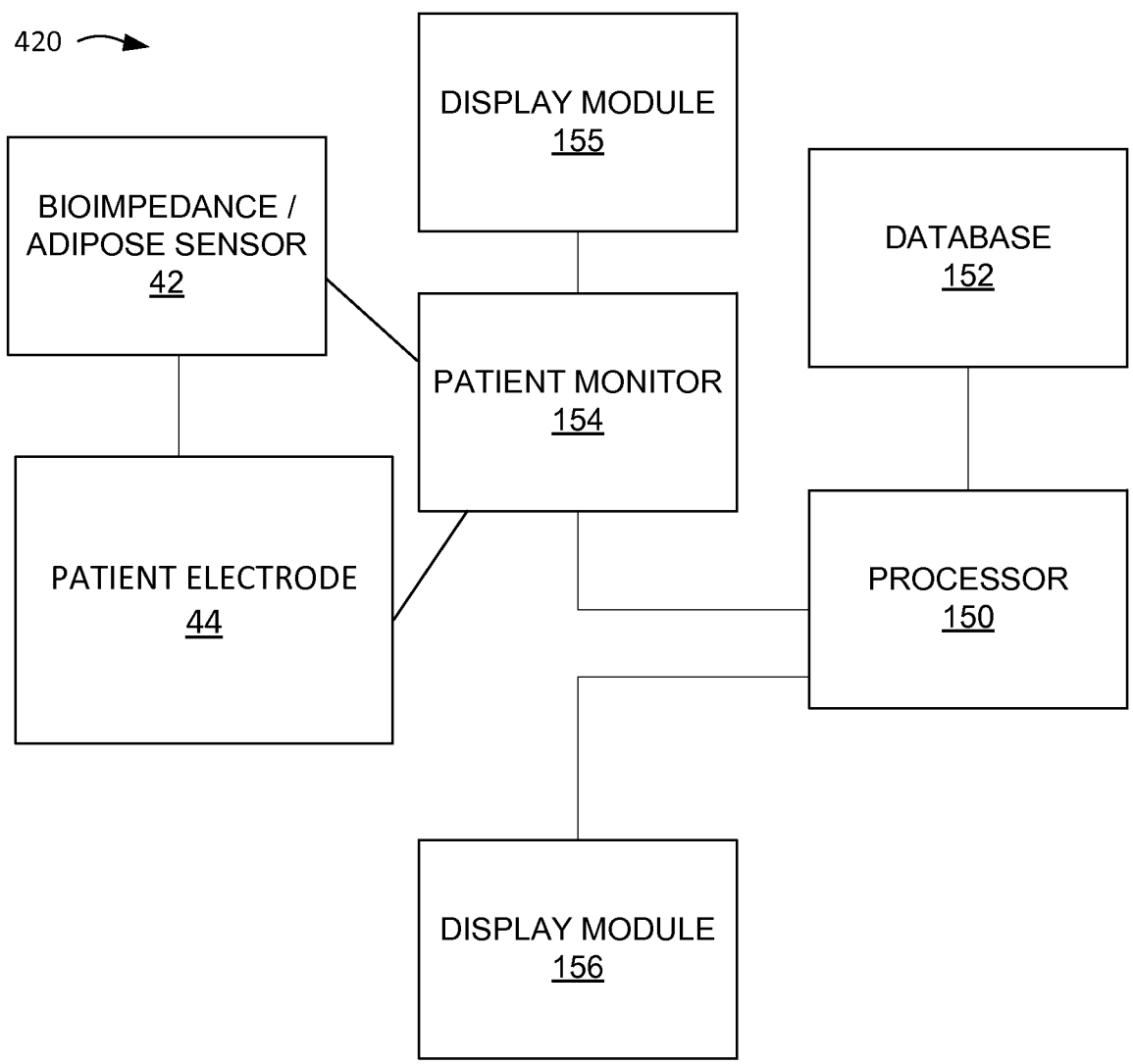
FIG. 4 illustrates a patient monitoring and control system including a patient electrode and bioimpedance sensor, according to embodiments of the present invention.

FIG. 4 illustrates a patient monitoring and control system 420 including a patient electrode 44 and bioimpedance sensor 42, according to embodiments of the present invention. The bioimpedance sensor 42 is communicably coupled with a patient monitor 154, which may be, for example, a defibrillator or an automatic external defibrillator, according to embodiments of the present invention. The patient monitor 154 is also is communicably coupled with a patient electrode 44. The patient electrode 44 is configured to apply defibrillation energy to a patient. Both the bioimpedance sensor 42 and the patient electrode 44 may include or otherwise be in communication with a processor 150. A database 152 may be used to store information and/or instructions or other software. For example, the database 152 can store information related to various body mass indices as related to pre-determined values for a wide array of patients' heights and weights. In addition, the database 152, in certain embodiments, can store body mass index values, in a lookup table, for different fat thicknesses. The lookup table can include body mass index values associated with a measured response to various frequencies of a radiation source, various amplitudes of a radiation source or a combination thereof. The processor 150 is configured to determine a tissue type and/or thickness based on a measurement by the bioimpedance sensor 42. The patient monitor 154 may have its own display module 155 in communication therewith, and/or the system 320 may include a separate display module 156, according to embodiments of the present invention.

As described above, the bioimpedance sensor 42 (in connection with the processor 150) estimates thickness of adipose tissue based on two or more electrodes that apply current, and measure the response of a patient's tissue to the applied current. The thickness of adipose tissue can alter the effectiveness of a defibrillation energy applied by the patient electrode 44. The database 152 also includes a lookup table that associates an estimate of adipose tissue with a value for a defibrillation energy. The processor 150 is configured to alter a defibrillation energy applied by the patient electrode 44 based on an estimate of the thickness of adipose tissue in connection with the defibrillation energy values stored in the database 152. In certain embodiments, the database 152 also includes a lookup table that associates an estimate of adipose tissue as determined by a spectral sensor, for example as described above with reference to FIG. 3, with a value for a defibrillation energy. The processor 150 is configured to alter a defibrillation energy applied by the patient electrode 44 based on an estimate of the thickness of adipose tissue in connection with the defibrillation energy values stored in the database 152.

Figure 5:
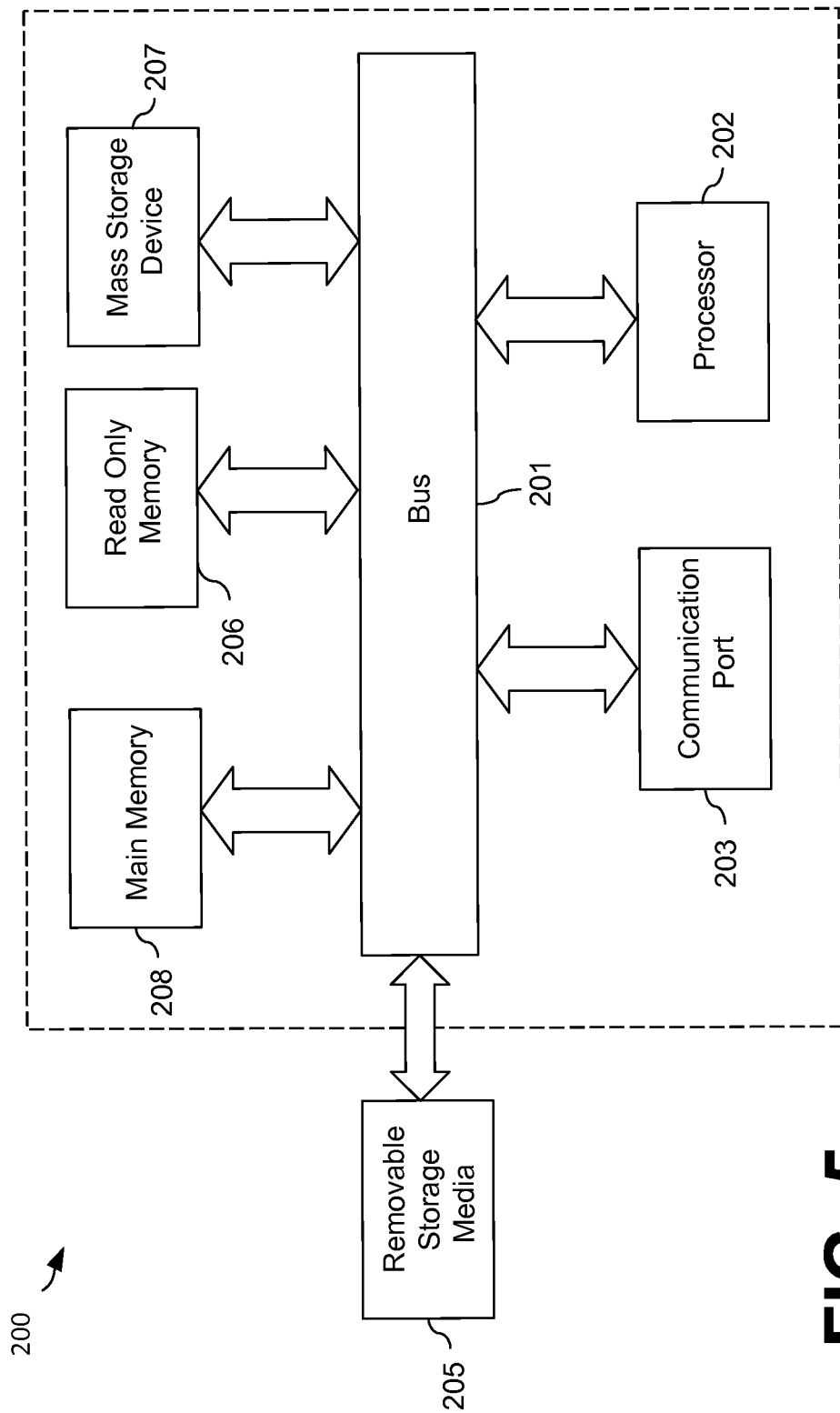
FIG. 5 illustrates a computer system, according to embodiments of the present invention.

FIG. 5 illustrates a computer system 200, according to embodiments of the present invention. The computer system 200 may be incorporated with, for example, a defibrillator and/or the display/control system of sensors described herein according to embodiments of the present invention. According to the present example, the computer system 200 includes a bus 201, at least one processor 202, at least one communication port 203, a main memory 206, a removable storage media 205, a read only memory 206, and a mass storage 207.

Processor(s) 202 can be any known processor, or any known microprocessor or processor for a mobile device. Communication port(s) 203 can be any of an RS-232 port for use with a modem based dialup connection, a copper or fiber 10/100/1000 Ethernet port, or a Bluetooth® or WiFi interface, for example. Communication port(s) 203 may be chosen depending on a network such a Local Area Network (LAN), Wide Area Network (WAN), or any network to which the computer system 200 connects. Main memory 206 can be Random Access Memory (RAM), or any other dynamic storage device(s) commonly known to one of ordinary skill in the art. Read only memory 206 can be any static storage device(s) such as Programmable Read Only Memory (PROM) chips for storing static information such as instructions for processor 202, for example.

Mass storage 207 can be used to store information and instructions. For example, flash memory or other storage media may be used, including removable or dedicated memory in a mobile or portable device, according to embodiments of the present invention. As another example, hard disks such as SCSI drives, an optical disc, an array of disks such as RAID, or any other mass storage devices may be used. Bus 201 communicably couples processor(s) 202 with the other memory, storage and communication blocks. Bus 201 can be a PCI/PCI-X or SCSI based system bus depending on the storage devices used, for example. Removable storage media 205 can be any kind of external hard-drives, floppy drives, flash drives, zip drives, compact disc-read only memory (CD-ROM), compact disc-re-writable (CD-RW), or digital video disk-read only memory (DVD-ROM), for example. The components described above are meant to exemplify some types of possibilities. In no way should the aforementioned examples limit the scope of the invention, as they are only exemplary embodiments of computer system 200 and related components.

FIG. 6 illustrates a bottom perspective view of a spectral sensor 600 having bioimpedance sensor electrodes 642, 643 and a spectral bench (14a-b and 16a-e), according to embodiments of the present invention. The spectral sensor 600 also includes a spectral detector 12 to measure the reflection (from a patient's tissue) of an illumination signal provided from one or more aspects of the spectral bench (14a-b and 16a-e). More specifically, the spectral bench includes two short-distance radiation sources 14a and 14b, and six long-distance radiation sources 16a, 16b, 16c, 16d, 16e, and 16f. Each of the sources are configured to produce illumination radiation at one or more frequency ranges. The short-distance radiation sources 14a and 14b, and six long-distance radiation sources 16a, 16b, 16c, 16d, 16e, and 16f, the spectral detector 12 and the bioimpedance sensor electrodes 642, 643 are shown as provided on a curved surface 11 of the spectral sensor 600 that interfaces with a patient's skin. The spectral sensor 600 is provided with openings 15 that allows a fastener such as a strap (e.g., a Velcro™ strap or another type of strap) to secure the spectral sensor 600 to a patient. As described in further detail above, the bioimpedance sensor electrodes 642, 643 and the spectral detector 12 (in connection with the short-distance radiation sources 14a and 14b, and six long-distance radiation sources 16a, 16b, 16c, 16d, 16e, and 16f) are provided to estimate a thickness of an adipose tissue layer between the spectral sensor 600 and the muscle tissue of a patient. Apertures 17a and 17b, formed in a side surface of housing 11, permit connection to communication interface and power source, respectively.

The spectral sensor 600 is also provided with a pressure sensor 650. In certain embodiments, it may be advantageous for a downward force to be applied to further force the spectral sensor 600 against a patient's skin. This additional force can compress fatty tissue of a patient. The additional force, however, can constrict blood vessels and negatively affect the ability of the spectral sensor to estimate a thickness of an adipose tissue layer between the spectral sensor 600 and the muscle tissue of a patient. The pressure sensor 650, in connection with processor circuitry, is configured to determine the pressure applied between the interface surface of the spectral sensor 600 and a patient's skin. The processor circuitry (described in detail above) calculates the applied pressure, and can intensify or alter a frequency or amplitude of an illumination signal provided by one or more of the short-distance radiation sources 14a and 14b, and six long-distance radiation sources 16a, 16b, 16c, 16d, 16e, and 16f. The correlation between pressure and a desired intensity or frequency of the illumination signal are stored in a database, and compared by the processor circuitry. An auditory or visual indicator on the spectral sensor 600 provides an indication to the user of the appropriate level of force based on a measurement from the pressure sensor 650. For instance, the auditory indicator can include a warning buzz if too much pressure is applied. In addition, the visual indicator can provide a green/yellow/red indication of the pressure applied.

Figure 7:
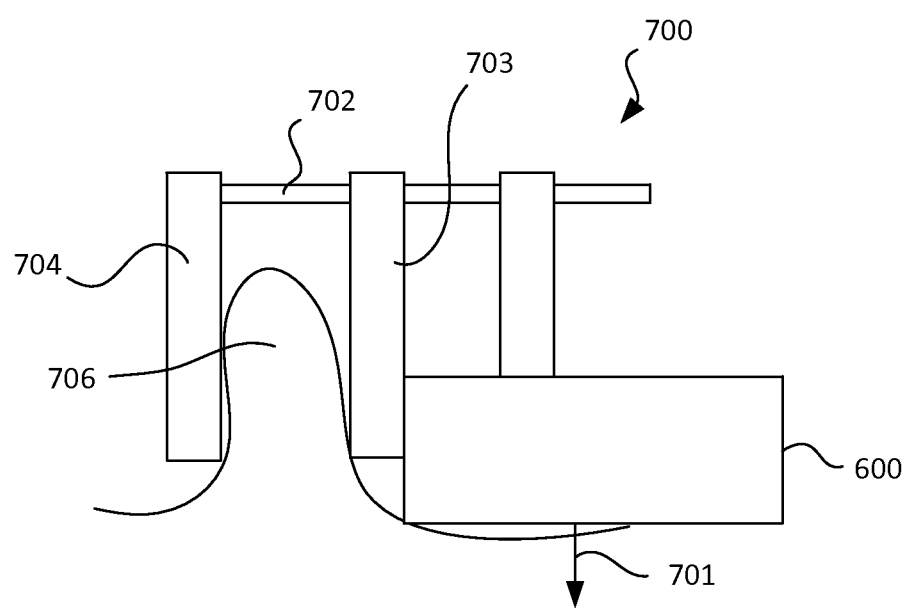
FIG. 7 illustrates a spectral sensor coupled with a body fat caliper device, according to embodiments of the present invention.

FIG. 7 illustrates a spectral sensor 600 coupled with a body fat caliper device 700, which may also be referred to as a mechanical adipose tissue sensor, according to embodiments of the present invention. The spectral sensor 600 is shown by the downward arrow 701 interfacing with a patient' skin. The body fat caliper device includes jaws 703, 704, and a measurement reading portion 702. The jaws 703, 704 of the caliper are shown including a fold of skin and the underlying layer of fat 706. The measurement reading portion 702 can be mechanical or electronic. For example, a mechanical measurement reading portion 702 may include a visible measurement indicator such as a ruler (e.g., as in the case of a vernier caliper), a rack and pinion that actuates a pointer (e.g., as in the case of a dial caliper), and/or the like. An electronic measurement reading portion 702 may include an analog and/or digital mechanism for obtaining measurements and may include an indicator such as a digital display. If the measurement reading portion 702 is mechanical, the spectral sensor 600 includes a manual input section for a user to input the measured fat level based on the caliper reading. If measurement reading portion 702 is electronic, the spectral sensor 600 can include a manual input section for a user to input the measured fat level based on the caliper reading, or alternatively, a communications connection is provided from the caliper to the spectral sensor 600 to automatically input the measured fat level. Based on the measured fat level, the spectral sensor 600 adjusts the estimate of a thickness of an adipose tissue layer between the spectral sensor 600 and the muscle tissue of a patient.

The connection between the spectral sensor 600 and the caliper can be provided by a wired connection such as via a USB cable, a copper or fiber wire, or an Ethernet cable, or a wireless connection such as a Bluetooth® or WiFi interface, according to embodiments of the present invention.

Figure 8:
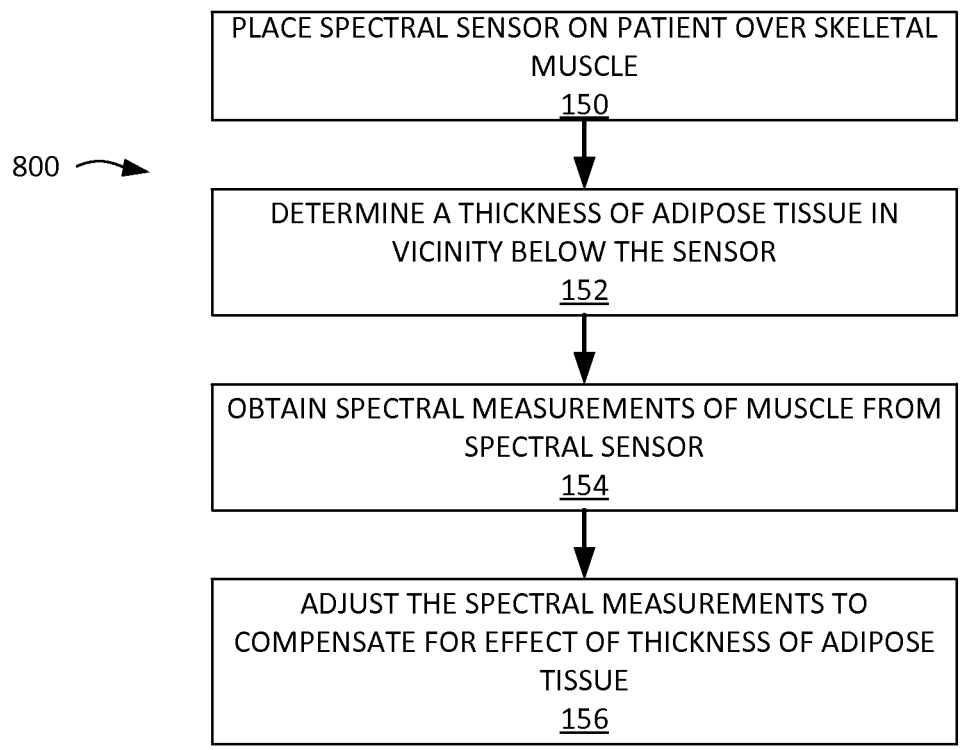
FIG. 8 depicts a flow chart illustrating a method for adjusting spectral measurements to compensate for adipose tissue, according to embodiments of the present invention.

FIG. 8 depicts a flow chart 800 illustrating a method for adjusting spectral measurements to compensate for adipose tissue, according to embodiments of the present invention. The method for adjusting spectral measurements to compensate for adipose tissue includes placing a spectral sensor 600 on a patient's skin above the patient's skeletal muscle (block 150), wherein the spectral sensor 600 comprises two or more long-distance radiation sources 16a-e, one or more short-distance radiation sources 14a-b, a spectral detector 12, and bioimpedance sensor electrodes 642, 643. The two or more long-distance radiation sources 16a-e and the one or more short-distance radiation sources 14a-b are located on the spectral sensor 600 at different distances from the spectral detector 12, wherein at least a portion of the spectral sensor 600 may have a convex outer profile for placement against a concave profile of the intercostal space, as illustrated in FIG. 6.

The method for adjusting spectral measurements to compensate for adipose tissue also includes determining a thickness of adipose tissue in vicinity below the sensor 600 (block 152). As described herein, this is determined by using one or more of the two or more long-distance radiation sources 16a-e, one or more short-distance radiation sources 14a-b, a spectral detector 12, and/or the bioimpedance sensor electrodes 642, 643. In addition, the method further includes obtaining spectral measurements of muscle from the spectral sensor 600 (block 154), and adjusting the spectral measurements to compensate for effect of the thickness of the adipose tissue (block 156).

Figure 9:
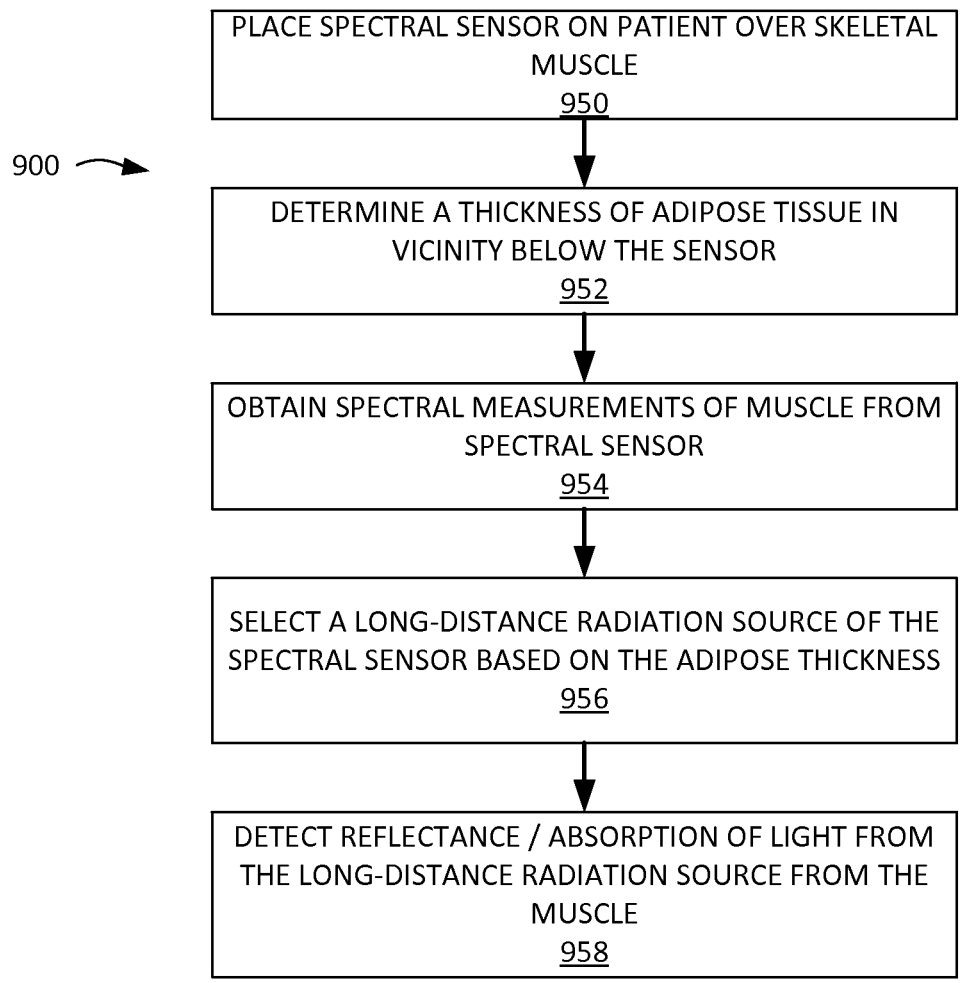
FIG. 9 depicts a flow chart illustrating a method for selecting a long distance radiation source for illumination of target tissue with a spectral sensor by determining a thickness of adipose tissue, according to embodiments of the present invention.

FIG. 9 depicts a flow chart 900 illustrating a method for selecting a long distance radiation source for illumination of target tissue with a spectral sensor 600 for determining a thickness of adipose tissue, according to embodiments of the present invention. The method for selecting a long-distance radiation source includes placing a spectral sensor 600 on a patient's skin in a first position in an intercostal space above the patient's myocardium (block 950), wherein the spectral sensor 600 comprises two or more long-distance radiation sources 16a-e, one or more short-distance radiation sources 14a-b, a spectral detector 12, and bioimpedance sensor electrodes 642, 643. The method for selecting a long-distance radiation source also includes determining a thickness of adipose tissue in vicinity below the sensor 600 (block 952). In addition, the method further includes obtaining spectral measurements of muscle from the spectral sensor 600 (block 954). The method may further include selecting a radiation source of the two or more long-distance radiation sources which most effectively illuminates tissue of the myocardium for determining adipose tissue thickens when the spectral sensor 600 (block 956). Finally, the method for selecting a long-distance radiation source includes detecting reflectance/absorption of light from the long-distance radiation source from the muscle (block 958).

Figure 10:
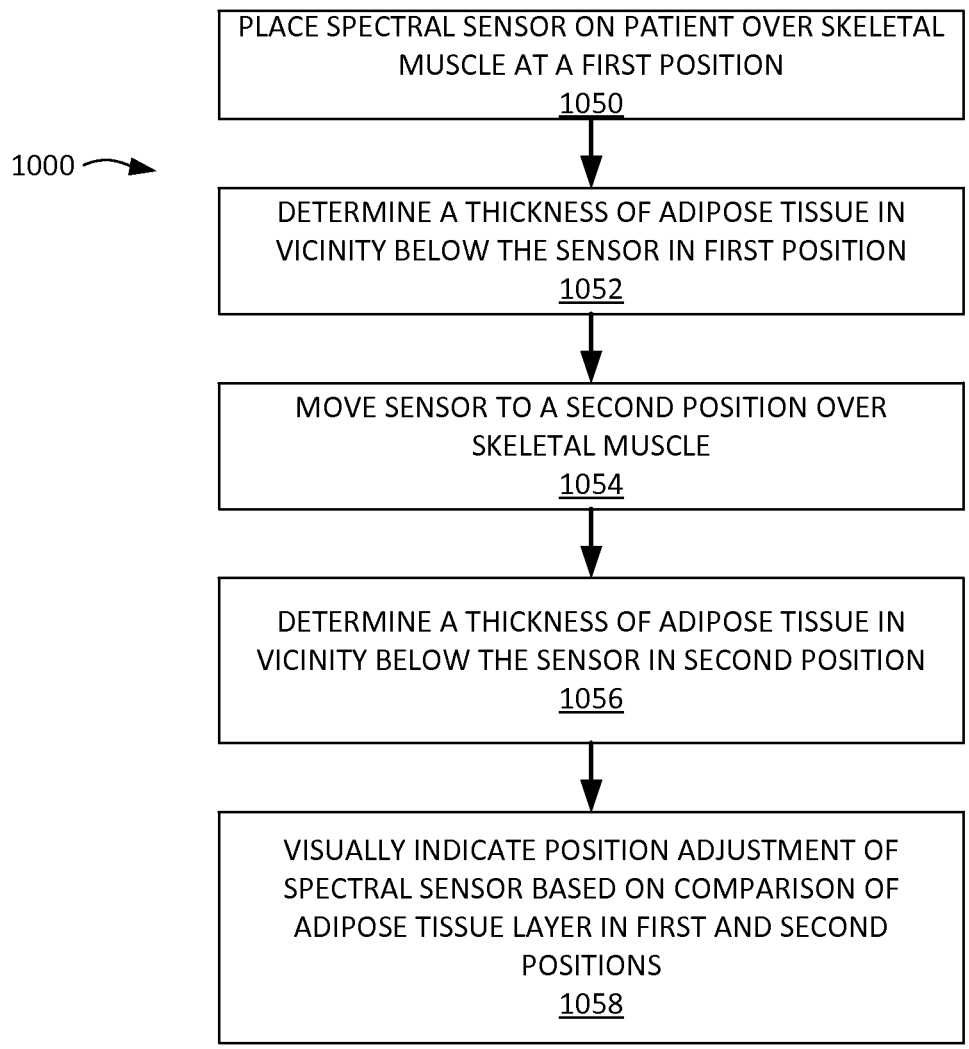
FIG. 10 depicts a flow chart illustrating a method for indicating position adjustment of a spectral sensor based on adipose tissue measurements.

FIG. 10 depicts a flow chart 1000 illustrating a method for indicating position adjustment of a spectral sensor 600 based on adipose tissue measurements. The method for indicating a position adjustment of a spectral sensor 600 includes placing a spectral sensor 600 on a patient's skin above the patient's muscle (block 1050), wherein the spectral sensor 600 comprises two or more long-distance radiation sources 16*a*-*e*, one or more short-distance radiation sources 14*a*-*b*, a spectral detector 12, and bioimpedance sensor electrodes 642, 643. The method for indicating a position adjustment of a spectral sensor 600 also includes determining a thickness of adipose tissue in vicinity below the sensor 600 (block 1052). The method may further include repositioning the spectral sensor 600 (block 1054) from the first position to a second position, and determining a thickness of adipose tissue (block 1056). The first thickness may be compared with the second thickness, and, based on the comparison, the sensor 600 may be configured to visually indicate a direction of position adjustment of the spectral sensor 600 to achieve more effective illumination of the tissue of the muscle in an area with a thinner adipose layer (block 1058).

Figure 11:
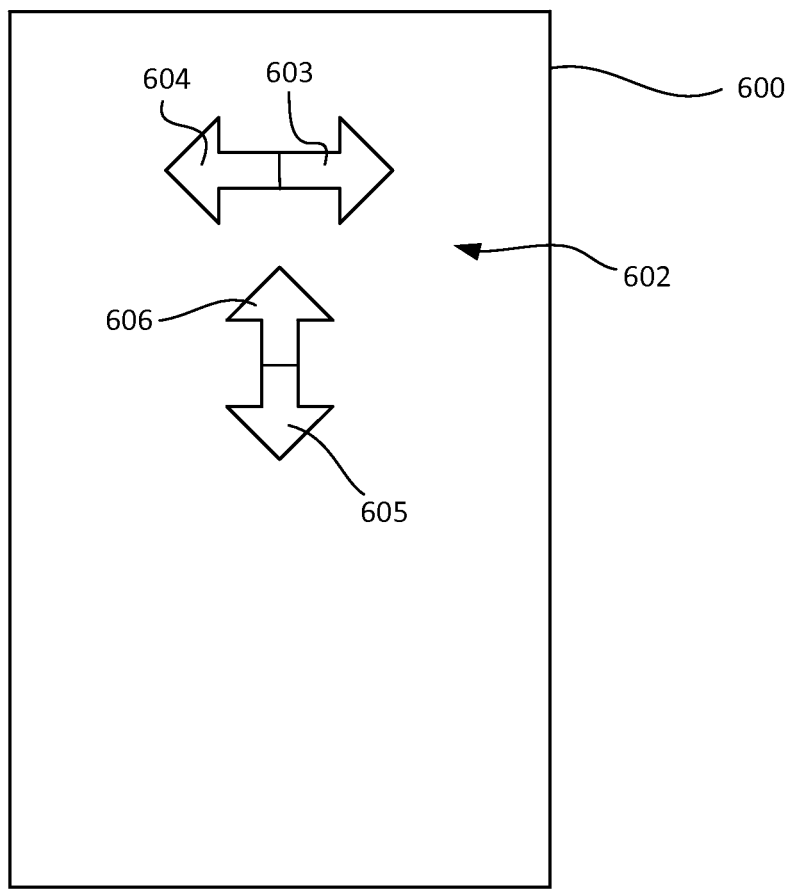
FIG. 11 illustrates a top plan view of a spectral sensor having visual indicators, according to embodiments of the present invention.

FIG. 11 illustrates a top plan view of a spectral sensor 600 having visual indicators 603-606, according to embodiments of the present invention. Based on the measured thickness of adipose tissue of a patient, the visual indicators 603-606 direct a user to an optimal positioning of the spectral sensor 600. For example, arrow 603 may be illuminated or its color changed or otherwise activated to indicate translation of the entire sensor 600 along a certain direction. The visual indicators 603-606 may take various forms, shapes, and arrangements, and one of ordinary skill in the art, based on the present disclosure, will appreciate that numerous other visual indicators may be used to achieve the described functionality.

The visual indicators may be lights, including for example light emitting diodes (LEDs). Different colors, and/or flashing patterns, and/or brightnesses may be employed. Further, audio and/or haptic feedback devices may be included, either in addition to or instead of visual indicators, to provide positioning and/or placement feedback.

Figure 12:
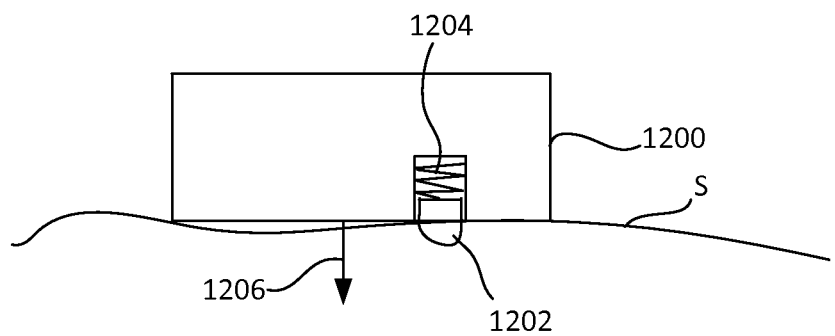
FIG. 12 illustrates a spectral sensor with a spring loaded probe for measuring body fat, according to embodiments of the present invention.

FIG. 12 illustrates another spectral sensor 1200, which may also be referred to as an optical spectroscope, which is placed onto the skin S of a patient, with the spectral bench facing toward the patient along direction 1206, according to embodiments of the present invention. Spectral sensor 1200, or its housing, includes a probe 1202 which is movable with respect to the sensor 1200 housing; for example, probe 1202 may be spring loaded onto or within housing 1200 with spring 1204. Probe 1202 is configured to interface with the user's skin to estimate a thickness of the adipose tissue beneath the skin. In some embodiments, the probe 1202 is spring loaded, and sensor 1200 measures the depth of deflection of the skin S with respect to the sensor 1200 in order to estimate a thickness of an adipose tissue layer below the skin S based on a known spring constant for spring 1204 and/or a known force provided by probe 1202 to skin. According to other embodiments, the probe 1202 is mechanically actuated, for example to punch momentarily into the skin to observe the acoustic, vibrational, and/or acceleration parameters experienced by the probe 1202, in order to determine the thickness of the adipose tissue layer below the skin S.

Figure 13:
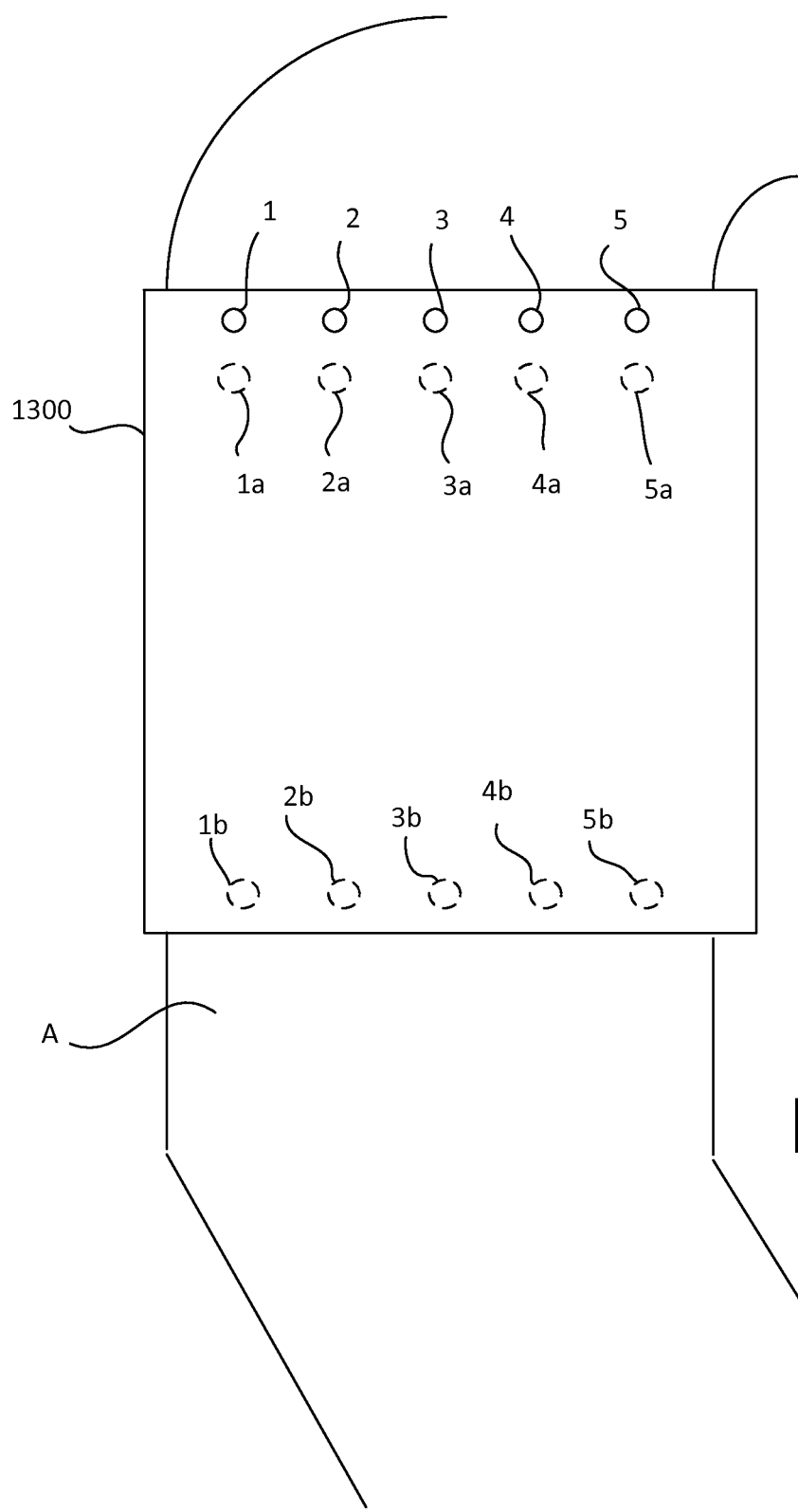
FIG. 13 illustrates an arm cuff with visual indicators corresponding to bioimpedance sensor placements, according to embodiments of the present invention.

FIG. 13 illustrates a device, such as a cuff 1300, which includes multiple sets of bioimpedance sensors placed on the side of the cuff 1300 facing the user's skin. This may include a first set of bioimpedance electrodes 1*a*, 1*b* to form a first bioimpedance sensor; a second set of bioimpedance electrodes 2*a*, 2*b* to form a second bioimpedance sensor; a third set of bioimpedance electrodes 3*a*, 3*b* to form a third bioimpedance sensor; a fourth set of bioimpedance electrodes 4*a*, 4*b* to form a fourth bioimpedance sensor; and fifth set of bioimpedance electrodes 5*a*, 5*b* to form a fifth bioimpedance sensor. The cuff 1300 may be configured to wrap around and/or encircle a limb or a portion of a limb, for example a user's arm A as shown in FIG. 13. On the outside or exterior of the cuff 1300 (e.g. the cuff 1300 as applied to the arm A), may be located visual indicators 1-5, with each visual indicator corresponding in location and/or placement to one of the bioimpedance sensors or electrode sets. For example, visual indicator 1 is located in alignment, for example circumferential alignment as shown in FIG. 13, with the bioimpedance sensor formed by electrodes 1*a*, 1*b*. The cuff 1300 may be configured to activate the bioimpedance sensors, either sequentially or simultaneously, to determine the best position along the cuff 1300, for example the best circumferential position along the cuff 1300, for placing the spectral sensor to correspond with the thinnest layer of adipose tissue, and/or thickest layer of muscle tissue, and/or the desired thicknesses of adipose tissue and muscle tissue at the given location. This "best" position may be indicated by the illumination of the visual indicator 1-5 associated with such position. For example, if the thinnest adipose tissue layer is measured or estimated to be along the bioimpedance sensor formed by electrodes 3*a*, 3*b*, then the visual indicator 3 may be activated. Visual indicators 1-5 may be light-emitting diodes (LEDs), for example, and their activation may involve illuminating them, for example with a constant illumination or according to a flashing sequence.

According to some embodiments, if the locations corresponding to visual indicators 3 and 4 have adipose tissue layers estimated to be equal or substantially equal, both visual indicators 3 and 4 may be illuminated, indicating that the user may wish to place a spectral sensor between the two visual indicators 3, 4. According to other embodiments, the signals from the bioimpedance sensors are used to make a yes/no determination about whether the adipose tissue layer at each location is too thick for a desired spectral sensor measurement, and the visual indicators 1-5 may each be activated independently to indicate either the yes or the no condition. A spectral sensor may be attached to the cuff 1300 and moved to the position corresponding to that which is visually indicated by the visual indicators 1-5, according to embodiments of the present invention. In some cases, the cuff 1300 features a cutout or a gap where the spectral sensor may be inserted and placed directly onto the user's skin, while the cuff 1300 also remains on the user's skin to indicate a desired spectral sensor placement.

A system for non-invasively measuring a physiologic status of tissue of a patient may include a housing 11, an optical spectroscope 600 at least partially disposed within the housing 11, the optical spectroscope 600 comprising at least one light source 14*a*-*b*, 16*a*-*e* capable of emitting light at a range of wavelengths, a wavelength-sensitive sensor 12 capable of detecting light intensity, at two or more distinct wavelengths, of light scattered and/or reflected by muscle tissue of the patient in order to measure a physiologic status of the muscle tissue; a bioimpedance sensor 642, 643 at least partially disposed within the housing 11, the bioimpedance sensor configured to generate a signal corresponding to an estimation of a thickness of an adipose tissue layer between the optical spectroscope and the muscle tissue; and a processor 150, 202 communicably coupled to a memory 206, the memory 206 including instructions that, when executed by the processor, cause the processor to (1) receive the estimations of the thickness generated upon placement of the housing 11 at two or more locations on the patient, (2) compare the estimations of the thickness, and (3) based on the comparison, generate a visual indication configured to assist in placement of the housing 11 toward or at a location corresponding to thickness of the adipose tissue layer that is smaller relative to surrounding thicknesses, for example by using visual indicators 603, 604, 605, 606 shown in FIG. 11, according to embodiments of the present invention.

The memory may further include instructions that, when executed by the processor 150, 202, cause the processor to generate the visual indication by illuminating the visual indicator 603, 604, 605, 606, which may also provide a directional and/or multidirectional indication (e.g. side-to-side movement indication and/or front-to-back movement indication as shown in FIG. 11).

The housing 11 may include at least one inertial sensor 160 communicably coupled with the processor 150 and configured to provide positioning or location information to the processor. The inertial sensor 160 may be or include, for example, an accelerometer and/or a gyroscope, according to embodiments of the present invention.

As illustrated in FIG. 13, for example, a system for non-invasively measuring a physiologic status of tissue of a patient may include a cuff 1300 configured to at least partially cover a portion of a limb A, a first bioimpedance sensor 1*a*, 1*b* disposed on the cuff 1300 so as to abut skin of the patient when the cuff at least partially covers the portion of the limb A, the first bioimpedance sensor 1*a*, 1*b* configured to generate a signal corresponding to an estimation of a thickness of an adipose tissue layer at a first location, a second bioimpedance sensor 2*a*, 2*b* disposed on the cuff 1300 so as to be separated from the first bioimpedance sensor 1*a*, 1*b* and to abut skin of the patient when the cuff at least partially covers the portion of the limb, the second bioimpedance sensor 2*a*, 2*b* configured to generate a signal corresponding to an estimation of a thickness of an adipose tissue layer at a second location, a first visual indicator 1 disposed on the cuff 1300 in manner corresponding to the first location, a second visual indicator 2 disposed on the cuff 1300 in a manner corresponding to the second location; and a processor 150, 202 communicably coupled to a memory 152, 206, the first and second bioimpedance sensors 1*a*, 1*b*, 2*a*, and 2*c*, and the first and second visual indicators 1, 2, the memory including instructions that, when executed by the processor, cause the processor to (1) receive the estimations of the thickness of the adipose tissue layer at the first and second locations, (2) compare the estimations of the thickness, and (3) based on the comparison, activating the first visual indicator 1 when the comparison indicates that the estimation of the thickness of the adipose tissue layer at the first location is lower than the estimation of the thickness of the adipose tissue layer at the second location.

As shown in FIG. 13, the first and second locations 1, 2 are circumferentially offset about the limb A when the cuff 1300 at least partially covers the portion of the limb A. FIG. 13 also illustrates that the first visual indicator 1 and the first bioimpedance sensor 1*a*, 1*b* are substantially aligned at a first circumferential position about the limb A when the cuff 1300 at least partially covers the portion of the limb, and the second visual indicator 2 and the second bioimpedance sensor 2*a*, 2*b* are substantially aligned at a second circumferential position about the limb A when the cuff 1300 at least partially covers the portion of the limb, with the first and second circumferential positions being offset circumferentially.

In some cases, the cuff 1300 may include an optical spectroscope configured for placement on the patient at the first location (e.g. the circumferential zone aligned or substantially aligned with bioimpedance sensor 1*a*, 1*b*) based on the activation of the first visual indicator 1. As illustrated in FIG. 13, the cuff 1300 may further include a third bioimpedance sensor 3*a*, 3*b* disposed on the cuff so as to be separated from the first and second bioimpedance sensors and to abut skin of the patient when the cuff at least partially covers the portion of the limb, the third bioimpedance sensor configured to generate a signal corresponding to an estimation of a thickness of an adipose tissue layer at a third location, a fourth bioimpedance sensor 4*a*, 4*b* disposed on the cuff so as to be separated from the first, second, and third bioimpedance sensors and to abut skin of the patient when the cuff at least partially covers the portion of the limb, the fourth bioimpedance sensor configured to generate a signal corresponding to an estimation of a thickness of an adipose tissue layer at a fourth location, and a fifth bioimpedance sensor 5*a*, 5*b* disposed on the cuff so as to be separated from the first, second, third, and fourth bioimpedance sensors and to abut skin of the patient when the cuff at least partially covers the portion of the limb, the fifth bioimpedance sensor configured to generate a signal corresponding to an estimation of a thickness of an adipose tissue layer at a fifth location, a third visual indicator 3 disposed on the cuff in manner corresponding to the third location, a fourth visual indicator 4 disposed on the cuff in a manner corresponding to the fourth location, and a fifth visual indicator 5 disposed on the cuff in a manner corresponding to the fourth location. The memory 152, 206 may further include instructions that, when executed by the processor 150, 202, cause the processor to (1) receive the estimations of the thickness of the adipose tissue layer at the third, fourth, and fifth locations, and (3) based on the comparison, activating the first visual indicator when the comparison indicates that the estimation of the thickness of the adipose tissue layer at the first location is lower than the estimation of the thickness of the adipose tissue layer at the second, third, fourth, and fifth locations.

A system for non-invasively measuring a physiologic status of tissue of a patient may include a housing 11, an optical spectroscope 600 at least partially disposed within the housing 11, the optical spectroscope 600 comprising at least one light source 14*a*-*b*, 16*a*-*e* capable of emitting light at a range of wavelengths, a wavelength-sensitive sensor 12 capable of detecting light intensity, at two or more distinct wavelengths, of light scattered and/or reflected by muscle tissue of the patient in order to measure a physiologic status of the muscle tissue; a mechanical adipose sensor 700, 1202 at least partially disposed on the housing 600, 1200, the mechanical adipose sensor configured to generate a signal corresponding to an estimation of a thickness of an adipose tissue layer between the optical spectroscope and the muscle tissue; and a processor 150, 202 communicably coupled to a memory 206, the memory 206 including instructions that, when executed by the processor, cause the processor to (1) receive the estimations of the thickness generated upon placement of the housing 11 at two or more locations on the patient, (2) compare the estimations of the thickness, and (3) based on the comparison, generate a visual indication configured to assist in placement of the housing 11 toward or at a location corresponding to thickness of the adipose tissue layer that is smaller relative to surrounding thicknesses, for example by using visual indicators 603, 604, 605, 606 shown in FIG. 11, according to embodiments of the present invention.

The memory may further include instructions that, when executed by the processor 150, 202, cause the processor to generate the visual indication by illuminating the visual indicator 603, 604, 605, 606, which may also provide a directional and/or multidirectional indication (e.g. side-to-side movement indication and/or front-to-back movement indication as shown in FIG. 11).

In some cases, the mechanical adipose sensor is a skin fold caliper 700, for example as shown in FIG. 7. In other cases, the mechanical adipose sensor is a spring loaded skin probe 1202, for example as shown in FIG. 12. In other cases, the mechanical adipose sensor is a tonometric sensor.

A system for non-invasively measuring a physiologic status of tissue of a patient may include a housing 11, an optical spectroscope 600 at least partially disposed within the housing 11, the optical spectroscope 600 comprising at least one light source 14*a-b*, 16*a-e* capable of emitting light at a range of wavelengths, a wavelength-sensitive sensor 12 capable of detecting light intensity, at two or more distinct wavelengths, of light scattered and/or reflected by muscle tissue of the patient in order to measure a physiologic status of the muscle tissue; an ultrasound sensor 42 at least partially disposed within the housing 11, the ultrasound sensor 42 configured to generate a signal corresponding to an estimation of a thickness of an adipose tissue layer between the optical spectroscope and the muscle tissue; and a processor 150, 202 communicably coupled to a memory 206, the memory 206 including instructions that, when executed by the processor, cause the processor to (1) receive the estimations of the thickness generated upon placement of the housing 11 at two or more locations on the patient, (2) compare the estimations of the thickness, and (3) based on the comparison, generate a visual indication configured to assist in placement of the housing 11 toward or at a location corresponding to thickness of the adipose tissue layer that is smaller relative to surrounding thicknesses, for example by using visual indicators 603, 604, 605, 606 shown in FIG. 11, according to embodiments of the present invention.

The memory may further include instructions that, when executed by the processor 150, 202, cause the processor to generate the visual indication by illuminating the visual indicator 603, 604, 605, 606, which may also provide a directional and/or multidirectional indication (e.g. side-to-side movement indication and/or front-to-back movement indication as shown in FIG. 11).

A system for non-invasively measuring a physiologic status of tissue of a patient may include a housing 11, an optical spectroscope 600 at least partially disposed within the housing 11, the optical spectroscope 600 comprising at least one light source 14*a-b*, 16*a-e* capable of emitting light at a range of wavelengths, a wavelength-sensitive sensor 12 capable of detecting light intensity, at two or more distinct wavelengths, of light scattered and/or reflected by muscle tissue of the patient in order to measure a physiologic status of the muscle tissue; a body mass index (BMI) calculator 42 at least partially disposed within the housing 11, the BMI calculator 42 configured to receive user input and to generate a signal corresponding to an estimation of a thickness of an adipose tissue layer between the optical spectroscope and the muscle tissue; and a processor 150, 202 communicably coupled to a memory 206, the memory 206 including instructions that, when executed by the processor, cause the processor to (1) receive the estimations of the thickness generated upon placement of the housing 11 at two or more locations on the patient, (2) compare the estimations of the thickness, and (3) based on the comparison, generate a visual indication configured to assist in placement of the housing 11 toward or at a location corresponding to thickness of the adipose tissue layer that is smaller relative to surrounding thicknesses, for example by using visual indicators 603, 604, 605, 606 shown in FIG. 11, according to embodiments of the present invention.

The memory may further include instructions that, when executed by the processor 150, 202, cause the processor to generate the visual indication by illuminating the visual indicator 603, 604, 605, 606, which may also provide a directional and/or multidirectional indication (e.g. side-to-side movement indication and/or front-to-back movement indication as shown in FIG. 11).

While FIG. 13 illustrates bioimpedance sensors 1*a*-5*b* placed at different circumferential locations about arm A, according to some embodiments of the invention various bioimpedance sensors may be placed at different locations about the body to determine which location would be the most ideal for placement of the spectral sensor 40. For example, bioimpedance pads could be placed on the patient's back, thigh(s), deltoid(s) and all be communicably coupled to a processor which determines or estimates the adipose tissue thickness at each location, according to embodiments of the present invention.

While various embodiments of the present invention are described with respect to an estimation of thickness of an adipose tissue layer, such estimation may be done in the form of estimating the thickness of a muscle tissue, and/or such estimation may be performed in addition to or instead of estimating the thickness of a muscle tissue. For example, processor 150 may look for a best frequency response of the tissue in a bioimpedance test to best match that of muscle tissue. According to some embodiments of the present invention, this frequency response may be compared against other locations on the patient and/or a control location (e.g. a known area of thick adipose tissue) on the patient with known muscle tissue properties, in order to comparatively determine an optimal location for placement of the sensor 40 and/or to visually direct the user to place the housing 11 at such location.

According to some embodiments of the present invention, the bioimpedance sensor(s) obtain a frequency response of the tissue over a range of frequencies, rather than at one or two frequencies such as 30 khz or 60 khz, in order to compare with known data, or control data for the patient, to determine the type of tissue and/or its depth profile below. According to some embodiments of the present invention, this includes the use of a complex impedance, capacitance, and/or resistance model to distinguish between muscle, bone, and fat.

Any of the sensors 10, 40, 600, 1200 described herein may include any or a subset of the hardware, software, characteristics, and/or performance of any of the spectral sensors and related functionality described in the '535 Publication, according to embodiments of the present invention.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A system for non-invasively determining a physiologic status of tissue of a patient, the system comprising:
   a housing;
   a spectral sensor at least partially disposed within the housing, the spectral sensor configured to determine a physiologic status of a muscle tissue of the patient;
   an adipose sensor at least partially disposed within the housing, the adipose sensor configured to estimate a thickness of an adipose tissue layer located between the spectral sensor and the muscle tissue, wherein the adipose sensor is independent of the spectral sensor; and a processor communicably coupled to a memory, the memory including instructions that, when executed by the processor, cause the processor to (1) receive the estimate of the thickness of the adipose tissue layer, and (2) assist a user in positioning of the spectral sensor at a location corresponding to a smaller thickness of the adipose tissue layer relative to a thickness of the adipose tissue layer surrounding the location based on the estimate of the thickness of the adipose tissue layer.

2. The system of claim 1, further comprising:
a cuff configured to at least partially cover a portion of a limb, wherein said adipose sensor is a first adipose tissue sensor disposed on the cuff so as to abut skin of the patient when the cuff at least partially covers the portion of the limb, the
    first adipose tissue sensor configured to generate a signal corresponding to an estimation of a thickness of an adipose tissue layer at a first location,
a second adipose tissue sensor disposed on the cuff so as to be separated from the first adipose tissue sensor and to abut skin of the patient when the cuff at least partially covers the portion of the limb, the second adipose tissue sensor configured to generate a signal corresponding to an estimation of a thickness of an adipose tissue layer at a second location,
a first visual indicator disposed on the cuff so as to visually correspond to the first location,
a second visual indicator disposed on the cuff so as to visually correspond to the second location; and
wherein the memory further includes instructions that, when executed by the processor, cause the processor to: (3) receive the estimate of the thickness of the adipose tissue layer from the second adipose tissue sensor, (4) compare the estimations of the thickness received from the first adipose tissue sensor and the second adipose tissue sensor, and (5) based on the comparison, activate the first visual indicator when the comparison indicates that the estimation of the thickness of the adipose tissue from the first adipose tissue sensor is lower than the estimation of the thickness of the adipose tissue layer from the second adipose tissue sensor.

3. The system of claim 2, wherein the first and second locations are circumferentially offset about the limb when the cuff at least partially covers the portion of the limb.

4. The system of claim 3, wherein the first visual indicator and the first adipose sensor are substantially aligned at a first circumferential position about the limb when the cuff at least partially covers the portion of the limb, and wherein the second visual indicator and the second adipose sensor are substantially aligned at a second circumferential position about the limb when the cuff at least partially covers the portion of the limb, and wherein the first and second circumferential positions are offset circumferentially.

5. The system of claim 2, further comprising an optical spectroscope, the optical spectroscope configured for placement on the patient at the first location based on the activation of the first visual indicator.

6. The system of claim 5, wherein the optical spectroscope is configured to determine a physiological status of a muscle tissue below the adipose tissue layer, and wherein the physiological status is one or more of: a pH of the muscle tissue, a muscle oxygen saturation, a blood hematocrit value of the muscle tissue, and a carbon dioxide concentration of the muscle tissue.

7. The system of claim 2, further comprising:
a third adipose sensor disposed on the cuff so as to be separated from the first and second adipose sensors and to abut skin of the patient when the cuff at least partially covers the portion of the limb, the third adipose sensor configured to generate a signal corresponding to an estimation of a thickness of an adipose tissue layer at a third location,
a fourth adipose sensor disposed on the cuff so as to be separated from the first, second, and third adipose sensors and to abut skin of the patient when the cuff at least partially covers the portion of the limb, the fourth adipose sensor configured to generate a signal corresponding to an estimation of a thickness of an adipose tissue layer at a fourth location;
a fifth adipose sensor disposed on the cuff so as to be separated from the first, second, third, and fourth adipose sensors and to abut skin of the patient when the cuff at least partially covers the portion of the limb, the fifth adipose sensor configured to generate a signal corresponding to an estimation of a thickness of an adipose tissue layer at a fifth location;
a third visual indicator disposed on the cuff so as to visually correspond to the third location,
a fourth visual indicator disposed on the cuff so as to visually correspond to the fourth location,
a fifth visual indicator disposed on the cuff so as to visually correspond to the fourth location; and
wherein the memory further includes instructions that, when executed by the processor, cause the processor to (1) receive the estimations of the thickness of the adipose tissue layer at the third, fourth, and fifth locations, and (3) based on the comparison, activating the first visual indicator when the comparison indicates that the estimation of the thickness of the adipose tissue layer at the first location is lower than the estimation of the thickness of the adipose tissue layer at the second, third, fourth, and fifth locations.

8. The system of claim 2, wherein the first and second adipose sensors are bioimpedance sensors.

9. The system of claim 1, wherein the memory includes instructions that, when executed by the processor, cause the processor to (1) receive the estimate of the thickness of the adipose tissue layer upon placement at two or more locations on the patient, and (2) compare the thickness of the adipose tissue layer at the two or more locations.

10. The system of claim 9, wherein the housing comprises at least one visual indicator disposed on or within the housing and wherein the processor is configured to activate the at least one visual indicator based upon the comparison of the thickness of the adipose tissue layer.

11. The system of claim 10, wherein the at least one visual indicator is configured to assist a user in placing the housing at the location corresponding to the smaller thickness of the adipose tissue layer relative to the thickness of the adipose tissue layer surrounding the location a smallest thickness of the adipose tissue layer.

12. The system of claim 11, wherein the visual indicator is a light source.

13. The system of claim 11, wherein the visual indicator is a multidirectional indicator.

14. The system of claim 1, wherein the spectral sensor comprises two or more long distance radiation sources and a spectral detector.

15. The system of claim 14, wherein the spectral sensor is further configured to determine the physiologic status of the muscle tissue of the patient by choosing one of the two or more long-distance radiation sources.

16. The system of claim 1, wherein the spectral sensor comprises one or more long distance radiation sources and a spectral detector.

17. The system of claim 16, wherein the spectral sensor is further configured to determine the physiologic status of the muscle tissue of the patient by focusing radiation emitted by one of the one or more long-distance radiation sources.

18. The system of claim 1, wherein the housing further comprises at least one inertial sensor communicably coupled with the processor and configured to provide positioning or location information to the processor.

19. The system of claim 18, wherein the inertial sensor comprises one or both of an accelerometer and a gyroscope.

20. The system of claim 1, wherein the adipose sensor is a bioimpedance sensor.

21. The system of claim 1, wherein the adipose sensor is an ultrasound sensor.

22. The system of claim 1, wherein the adipose sensor is mechanical adipose sensor.

23. The system of claim 1, wherein the adipose sensor comprises a body mass index calculator.

24. The system of claim 1, wherein the physiological status of the tissue is one or more of: a pH of the muscle tissue, a muscle oxygen saturation, a blood hematocrit value of the muscle tissue, and a carbon dioxide concentration of the muscle tissue.

25. The system of claim 1, wherein the adipose sensor is a bioimpedance sensor.

26. The system of claim 1, wherein the adipose sensor is an ultrasound sensor.

27. The system of claim 1, wherein the adipose sensor is a mechanical adipose sensor.

28. The system of claim 1, wherein the adipose sensor comprises a body mass index calculator.

29. The system of claim 1, wherein the physiologic status of the muscle tissue is one or more of: a pH of the muscle tissue, a muscle oxygen saturation, a blood hematocrit value of the muscle tissue, and a carbon dioxide concentration of the muscle tissue.

* * * * *

UNITED STATES PATENT AND TRADEMARK OFFICE
CERTIFICATE OF CORRECTION

PATENT NO. : 10,799,177 B2
APPLICATION NO. : 15/077385
DATED : October 13, 2020
INVENTOR(S) : Gary A. Freeman et al.

It is certified that error appears in the above-identified patent and that said Letters Patent is hereby corrected as shown below:

In the Specification

Column 1, Line 9, after "Ser.", insert -- No. --

In the Claims

Column 21, Line 22, Claim 2, delete "location," and insert -- location; --

Column 21, Line 29, Claim 2, delete "location," and insert -- location; --

Column 21, Line 31, Claim 2, delete "location," and insert -- location; --

Column 22, Line 8, Claim 7, delete "location," and insert -- location; --

Column 22, Line 24, Claim 7, delete "location," and insert -- location; --

Column 22, Line 26, Claim 7, delete "location," and insert -- location; --

Column 22, Line 28, Claim 7, delete "fourth" and insert -- fifth --

Column 22, Line 53, Claim 11, delete "to the" and insert -- to a --

Column 22, Line 55, Claim 11, delete "a smallest" and insert -- of the smaller --

Signed and Sealed this
Fourth Day of January, 2022

Drew Hirshfeld
*Performing the Functions and Duties of the*
*Under Secretary of Commerce for Intellectual Property and*
*Director of the United States Patent and Trademark Office*